(12) United States Patent
Goodall et al.

(10) Patent No.: US 7,486,988 B2
(45) Date of Patent: Feb. 3, 2009

(54) METHOD AND SYSTEM FOR ADAPTIVE VISION MODIFICATION

(75) Inventors: Eleanor V. Goodall, Seattle, WA (US); W. Daniel Hillis, Encino, CA (US); Roderick A. Hyde, Livermore, CA (US); Muriel Y. Ishikawa, Livermore, CA (US); Edward K. Y. Jung, Bellevue, WA (US); Nathan P. Myhrvold, Medina, WA (US); Lowell L. Wood, Jr., Livermore, CA (US)

(73) Assignee: Searete LLC, Bellevue, WA (US)

( * ) Notice: Subject to any disclaimer, the term of this patent is extended or adjusted under 35 U.S.C. 154(b) by 203 days.

(21) Appl. No.: 11/004,731

(22) Filed: Dec. 3, 2004

(65) Prior Publication Data
US 2006/0122531 A1 Jun. 8, 2006

(51) Int. Cl.
| | |
|---|---|
| A61B 5/04 | (2006.01) |
| A61B 13/00 | (2006.01) |
| A61B 3/00 | (2006.01) |
| A61B 3/10 | (2006.01) |
| G02F 1/1335 | (2006.01) |
| G02C 7/06 | (2006.01) |
| G02C 7/02 | (2006.01) |
| G02C 5/00 | (2006.01) |
| G02B 1/06 | (2006.01) |
| G02B 3/12 | (2006.01) |

(52) U.S. Cl. .............. 600/546; 600/372; 600/382; 600/383; 600/544; 600/545; 600/558; 600/546; 349/13; 351/168; 351/177; 351/211; 351/219; 351/200; 351/41; 359/665; 359/666

(58) Field of Classification Search .......... 600/372, 600/382, 383, 544, 545, 546, 558; 349/13; 351/168, 177, 211, 219, 200, 41; 359/665, 359/666
See application file for complete search history.

(56) References Cited

U.S. PATENT DOCUMENTS

| | | | |
|---|---|---|---|
| 3,161,718 | A | 12/1964 | DeLuca |
| 3,245,315 | A | 4/1966 | Marks et al. |
| 3,507,988 | A | 4/1970 | Holmes |
| 3,614,215 | A | 10/1971 | Mackta |
| 3,738,734 | A | 6/1973 | Tait et al. |
| 3,819,256 | A | 6/1974 | Bellows et al. |
| 4,168,882 | A | 9/1979 | Hopkins |

(Continued)

FOREIGN PATENT DOCUMENTS

DE WO 02/097511 A1 5/2001

OTHER PUBLICATIONS

Jacko, Julie A.; "Visual Dysfunction and Human-Computer Interaction"; pp. 1-2; ERCIM News No. 46, bearing a date of Jul. 2001; located at http://ercim.org/publication Ercim_News/enw46/jacko.html; printed on Dec. 13, 2004.

(Continued)

*Primary Examiner*—Max Hindenburg
*Assistant Examiner*—Jeffrey G Hoekstra

(57) ABSTRACT

Methods and systems for modifying or enhancing vision are described. In exemplary embodiments, neural or neuromuscular activity is analyzed to determine a focus or other quality of a visual input, and the focus or quality information used as a basis for controlling an adjustable lens system or optical system.

16 Claims, 12 Drawing Sheets

U.S. PATENT DOCUMENTS

| | | |
|---|---|---|
| 4,174,156 A | 11/1979 | Glorieux |
| 4,181,408 A | 1/1980 | Senders |
| 4,190,330 A | 2/1980 | Berreman |
| 4,255,023 A | 3/1981 | House |
| 4,261,655 A | 4/1981 | Honigsbaum |
| 4,264,154 A | 4/1981 | Petersen |
| 4,279,474 A | 7/1981 | Belgorod |
| 4,300,818 A | 11/1981 | Schachar |
| 4,373,218 A | 2/1983 | Schachar |
| 4,395,736 A | 7/1983 | Fraleux |
| 4,403,840 A | 9/1983 | Okun |
| 4,418,990 A | 12/1983 | Gerber |
| 4,429,959 A | 2/1984 | Walters |
| 4,444,471 A | 4/1984 | Ford, Jr. et al. |
| 4,466,705 A | 8/1984 | Michelson |
| 4,466,706 A | 8/1984 | Lamothe, II |
| 4,500,180 A | 2/1985 | Stevens |
| 4,564,267 A | 1/1986 | Nishimoto |
| 4,572,616 A | 2/1986 | Kowel et al. |
| 4,601,545 A | 7/1986 | Kern |
| 4,609,824 A | 9/1986 | Munier et al. |
| 4,697,598 A | 10/1987 | Bernard et al. |
| 4,709,996 A | 12/1987 | Michelson |
| 4,756,605 A | 7/1988 | Okada et al. |
| 4,772,094 A | 9/1988 | Sheiman |
| 4,787,903 A | 11/1988 | Grendahl |
| 4,795,248 A | 1/1989 | Okada et al. |
| 4,818,095 A | 4/1989 | Takeuchi |
| 4,836,652 A | 6/1989 | Oishi et al. |
| 4,842,601 A | 6/1989 | Smith |
| 4,844,086 A | 7/1989 | Duffy |
| 4,904,063 A | 2/1990 | Okada et al. |
| 4,907,860 A | 3/1990 | Noble |
| 4,919,520 A | 4/1990 | Okada et al. |
| 4,927,241 A | 5/1990 | Kuijk |
| 4,945,242 A | 7/1990 | Berger et al. |
| 4,952,788 A | 8/1990 | Berger et al. |
| 4,953,968 A | 9/1990 | Sherwin et al. |
| 4,955,389 A | 9/1990 | Schneider |
| 4,961,639 A | 10/1990 | Lazarus |
| 4,968,127 A | 11/1990 | Russell et al. |
| 4,974,602 A | 12/1990 | Abraham-Fuchs et al. |
| 4,981,342 A | 1/1991 | Fiala |
| 4,991,951 A | 2/1991 | Mizuno et al. |
| 5,015,086 A | 5/1991 | Okaue et al. |
| 5,020,538 A | 6/1991 | Morgan et al. |
| 5,052,401 A | 10/1991 | Sherwin |
| 5,066,301 A | 11/1991 | Wiley |
| 5,073,021 A | 12/1991 | Marron |
| 5,076,665 A | 12/1991 | Petersen |
| 5,091,801 A | 2/1992 | Ebstein |
| 5,108,169 A | 4/1992 | Mandell |
| 5,108,429 A | 4/1992 | Wiley |
| 5,142,411 A | 8/1992 | Fiala |
| 5,171,266 A | 12/1992 | Wiley et al. |
| 5,182,585 A | 1/1993 | Stoner |
| 5,184,156 A | 2/1993 | Black et al. |
| 5,187,672 A | 2/1993 | Chance et al. |
| 5,203,788 A | 4/1993 | Wiley |
| 5,208,688 A | 5/1993 | Fergason et al. |
| 5,229,885 A | 7/1993 | Quaglia |
| 5,239,412 A | 8/1993 | Naka et al. |
| 5,306,926 A | 4/1994 | Yonemoto |
| 5,309,095 A | 5/1994 | Ahonen et al. |
| 5,323,777 A | 6/1994 | Ahonen et al. |
| 5,324,930 A | 6/1994 | Jech, Jr. |
| 5,329,322 A | 7/1994 | Yancey |
| 5,351,100 A | 9/1994 | Schwenzfeier et al. |
| 5,352,886 A | 10/1994 | Kane |
| 5,359,444 A | 10/1994 | Piosenka et al. |
| 5,382,986 A | 1/1995 | Black et al. |
| 5,440,357 A | 8/1995 | Quaglia |
| 5,443,506 A | 8/1995 | Garabet |
| 5,451,766 A | 9/1995 | Van Berkel |
| 5,488,439 A | 1/1996 | Weltmann |
| 5,491,583 A | 2/1996 | Robb |
| 5,526,067 A | 6/1996 | Cronin et al. |
| 5,627,674 A | 5/1997 | Robb |
| 5,629,747 A | 5/1997 | Miyake |
| 5,629,790 A | 5/1997 | Neukermans et al. |
| 5,644,374 A | 7/1997 | Mukaiyama et al. |
| 5,654,786 A | 8/1997 | Bylander |
| 5,655,534 A | 8/1997 | Ilmoniemi |
| 5,684,637 A | 11/1997 | Floyd |
| 5,687,291 A | 11/1997 | Smyth |
| 5,712,721 A | 1/1998 | Large |
| 5,728,155 A | 3/1998 | Anello et al. |
| 5,739,959 A | 4/1998 | Quaglia |
| 5,748,382 A | 5/1998 | Maguire, Jr. |
| 5,777,719 A | 7/1998 | Williams et al. |
| 5,792,051 A | 8/1998 | Chance |
| 5,815,233 A | 9/1998 | Morokawa et al. |
| 5,840,040 A | 11/1998 | Altschuler et al. |
| 5,853,370 A | 12/1998 | Chance et al. |
| 5,861,936 A * | 1/1999 | Sorensen .................. 351/200 |
| 5,900,720 A | 5/1999 | Kallman et al. |
| 5,949,521 A | 9/1999 | Williams et al. |
| 5,956,183 A | 9/1999 | Epstein et al. |
| 5,973,852 A | 10/1999 | Task |
| 5,980,037 A | 11/1999 | Conway |
| 5,995,857 A | 11/1999 | Toomim et al. |
| 6,013,101 A * | 1/2000 | Israel ...................... 623/6.43 |
| 6,014,582 A | 1/2000 | He |
| 6,033,073 A * | 3/2000 | Potapova et al. ............ 351/211 |
| 6,066,084 A | 5/2000 | Edrich et al. |
| 6,069,742 A | 5/2000 | Silver |
| 6,120,538 A | 9/2000 | Rizzo, III et al. |
| 6,177,800 B1 | 1/2001 | Kubby et al. |
| 6,195,576 B1 | 2/2001 | John |
| 6,199,986 B1 | 3/2001 | Williams et al. |
| 6,212,015 B1 | 4/2001 | Heimer |
| 6,227,667 B1 | 5/2001 | Halldorsson et al. |
| 6,233,480 B1 | 5/2001 | Hochman et al. |
| 6,256,531 B1 | 7/2001 | Ilmoniemi et al. |
| 6,288,846 B1 | 9/2001 | Stoner, Jr. |
| 6,318,857 B1 * | 11/2001 | Shirayanagi ................. 351/41 |
| 6,325,508 B1 | 12/2001 | Decreton et al. |
| 6,352,345 B1 | 3/2002 | Zolten |
| 6,369,954 B1 | 4/2002 | Berge et al. |
| 6,370,414 B1 | 4/2002 | Robinson |
| 6,379,989 B1 | 4/2002 | Kubby et al. |
| 6,397,099 B1 | 5/2002 | Chance |
| 6,399,405 B1 | 6/2002 | Chen et al. |
| 6,445,509 B1 | 9/2002 | Alden |
| 6,491,394 B1 | 12/2002 | Blum et al. |
| 6,517,203 B1 | 2/2003 | Blum et al. |
| 6,523,954 B1 | 2/2003 | Kennedy et al. |
| 6,523,955 B1 | 2/2003 | Eberl et al. |
| 6,542,309 B2 | 4/2003 | Guy |
| 6,544,170 B1 | 4/2003 | Kajihara et al. |
| 6,580,858 B2 | 6/2003 | Chen et al. |
| 6,615,074 B2 | 9/2003 | Mickle et al. |
| 6,619,799 B1 | 9/2003 | Blum et al. |
| 6,647,296 B2 | 11/2003 | Fischell et al. |
| 6,655,035 B2 | 12/2003 | Ghandi et al. |
| 6,658,179 B2 | 12/2003 | Kubby et al. |
| 6,690,959 B2 | 2/2004 | Thompson |
| 6,694,180 B1 | 2/2004 | Boesen |
| 6,697,660 B1 | 2/2004 | Robinson |
| 6,709,108 B2 | 3/2004 | Levine et al. |
| 6,715,876 B2 | 4/2004 | Floyd |
| 6,733,130 B2 | 5/2004 | Blum et al. |
| 6,744,550 B2 | 6/2004 | Neukermans et al. |
| 6,747,806 B2 | 6/2004 | Gelbart |

| | | | |
|---|---|---|---|
| 6,752,499 | B2 | 6/2004 | Aller |
| 6,762,867 | B2 | 7/2004 | Lippert et al. |
| 6,768,246 | B2 | 7/2004 | Pelrine et al. |
| 2002/0036750 | A1 | 3/2002 | Eberl et al. |
| 2002/0140899 | A1 | 10/2002 | Blum et al. |
| 2002/0140902 | A1 | 10/2002 | Guirao et al. |
| 2003/0014091 | A1 | 1/2003 | Rastegar et al. |
| 2003/0158587 | A1 | 8/2003 | Esteller et al. |
| 2003/0165648 | A1 | 9/2003 | Lobovsky et al. |
| 2003/0231293 | A1 | 12/2003 | Blum et al. |
| 2004/0051846 | A1 | 3/2004 | Blum et al. |
| 2004/0056986 | A1 | 3/2004 | Blum et al. |
| 2005/0036109 | A1 | 2/2005 | Blum et al. |
| 2006/0028734 | A1 | 2/2006 | Kuiper et al. |
| 2006/0095128 | A1 | 5/2006 | Blum et al. |
| 2006/0238701 | A1 | 10/2006 | Blum |

OTHER PUBLICATIONS

Firelily Designs; "Color Vision, Color Deficiency"; pp. 1-12; located at http://firelily.com/opinions/color.html; printed on Dec. 13, 2004; bearing a Copyright date of 1996-2003.

FVM: Program Abstracts; "Program Abstracts"; pp. 1-25; located at http://www.cvs.rochester.edu/fvm_progabst.html; printed on Dec. 13, 2004.

Reuters; "'Thinking Cap' Controls Computer in New Experiment"; p. 1 of 1; located at http://www.reuters.com/printerFriendlyPopup.jhtml?type=topNews&StoryID=701077; printed on Dec. 13, 2004; bearing a date of 2004.

Carandini, Matteo; Heeger, David J.; Senn, Walter; "A Synaptic Explanation of Suppression in Visual Cortex"; The Journal of Neuroscience; bearing a date of Nov. 15, 2002; vol. 22.; pp. 10053-10065.

Center for Adaptive Optics: "How Does an Adaptive Optics System Work?"; bearing a date of 2002; pp. 1-2., located at : http://www.cfao.ucolick.org/ao/how.php , printed on Jul. 14, 2004.

Center for Adaptive Optics: "Other AO Primers"; bearing a date of 2002; pp. 1, located at http://www.cfaco.ucolick.org/ao/other.php , printed on Jul. 14, 2004.

Chance, Britton; Nioka, Shoko; Chen, Yu; "Shining New Light on Brain Function"; Spie's oemagazine; bearing a date of Jul. 2003; pp. 16-19 with 1 sheet of figures.

Croft, Mary Ann; Kaufman, Paul L.; Crawford, Kathryn S.; Neider, Michael W.; Glasser, Adrian; Bito, Laszlo Z.; "Accommodation dynamics in aging rhesus monkeys"; bearing a date of 1998; pp. 1885-1897.

Fantini, Sergio; Franceschini, Maria Angela; Gratton, Enrico; Hueber, Dennis; Rosenfeld, Warren; Maulik, Dev; Stubblefield, Phillip G.; Stankovic, Miljan R.; "Non-invasive optical mapping of the piglet brain in real time"; Optics Express; bearing dates of: Mar. 9, 1999; Apr. 7, 1999; Apr. 12, 1999; vol. 4, No. 8; pp. 308-314.

Fantini, Sergio; Heffer, Erica L.; Franceschini, Maria Angela; Gotz, Linda; Heinig, Anke; Heywang-Kobrunner, Sylvia; Schutz, Oliver; Siebold, Horst; "Optical Mammography with Intensity-Modulated Light"; pp. 1-7; printed on Aug. 30, 2004.

Gratton, Gabriele; Fabiani, Monica; Corballis, Paul M.; Hood, Donald C.; Goodman-Wood, Marsha R.; Hirsch, Joy; Kim, Karl; Friedman, David; Gratton, Enrico; "Fast and Localized Event-Related Optical Signals (EROS) in the Human Occipital Cortex: Comparisons with the Visual Evoked Potential and fMRI"; Neuroimage 6; bearing a date of 1997 and Dec. 24, 1996; pp. 168-180 ; Article No. NI970298.

Heeger, David J.; "Linking visual perception with human brain activity"; Current Opinion in Neurobiology; bearing a date of 1999, 9; pp. 474-479; located at: http://biomednet.com/elecref/0959438800900474.

Heeger, David; "Recent Publications"; printed on Sep. 30, 2004; pp. 1-20; located at: http://www.cns.nyu.edu/~david/publications.html.

Heeger, David J.; Ress, David; "What Does fMRI Tell Us About Neuronal Activity?"; Feb. 2002; vol. 3; pp. 142-151; located at: www.nature.com/reviews/neuro.

Intes, X.; Chance, B.; Holboke, M.J.; Yodh, A.G.; "Interfering diffusive photon-density waves with an absorbing-flourescent inhomogeneity"; Optics Express; bearing dates of Nov. 9, 2000, Jan. 17, 2001 and Jan. 29, 2001; vol. 8, No. 3; pp. 223-231.

Intes, X.; Ntziachristos, V.; Chance B.; "Analytical model for dual-interfering sources diffuse optical tomography"; Optics Express; bearing dates of Sep. 19, 2001, Dec. 14, 2001 and Jan. 14, 2002; vol. 10, No. 1; pp. 2-14.

Krulevitch, Peter; Bierden, Paul; Bifano, Thomas; Carr, Emily; Diams, Clara; Dyson, Harold; Helmbrecht, Michael; Kurczynski, Peter; Muller, Richard; Olivier, Scot; Peter, Yves-Alain; Sadoulet, Bernard; Solgaard, Olav; and Yang, E.H.; "MOEMS spatial light modulator development at the Center for Adaptive Optics"; bearing a date of 2003; pp. 227-234.

Lewotsky, Kristin; "Seeing into the Body"; Spie's OEMagazine; bearing a date of Jul. 2003; p. 15.

Makeig, Scott; Westerfield, Marissa; Townsend, Jeanne; Jung, Tzyy-Ping; Courchesne, Eric; Sejnowski,Terrence J.; "Functionally Independent Componenets of Early Event-Related Potentials in a Visual Spatial Attention Task"; Philosophical Transactions of the Royal Society; Biological Sciences: 354: 1135-44; bearing a date of Jun. 5, 1999; pp. 1-23.

Malonek, Dov; Dirnagl, Ulrich; Lindauer, Ute; Yamada, Katsuya; Kanno, Iwao; Grinvald, Amiram; "Vascular imprints of neuronal activity: Relationships between the dynamics of cortical blood flow, oxygenation, and volume changes following sensory stimulation"; Proc. Natl. Acad. Sci. USA, Neurobiology; bearing dates of Oct. 24, 1997; Jun. 9, 1997; and Dec. 1997; vol. 94; pp. 14826-14831.

Morgan, S.P.; Yong, K.Y.; "Controlling the phase response of a diffusive wave phased array system"; Optics Express; bearing dates of Oct. 19, 2000, Dec. 7, 2000, and Dec. 18, 2000; Vo. 7, No. 13; pp. 540-546.

Neri, Peter; Heeger, David J.; "Spatiotemporal mechanisms for detecting and identifying image features in human vision"; Nature Neuroscience; bearing dates of Jul. 8, 2002 and Aug. 2002; vol. 5, No. 8; pp. 812-816.

Photonics at imperial College; Applied Optics: "Wavefront sensing of the human eye"; "The double-pass process"; printed on Jul. 14, 2004; pp. 1; located at: http://op.ph.ic.ac.uk/research/index.html.

Photonics at Imperial College; Applied Optics: "Wavefront sensing of the human eye"; "Single-pass measurement of the wave aberration of the human eye"; bearing a date of Jul. 14, 2004; pp. 1-2; printed on Jul. 14, 2004; located at: http://op.ph.ic.ac.uk/research/index.html.

R&D Where Innovation Begins; editorial: "Vision Correction for the 21st Century"; printed on Aug. 30, 2004; pp. 1-3; located at: http://www.rdmag.com/Scripts/ShowPR.asp?PUBCODE=014&ACCT=1400000100&ISSUE=0401&RELTYPE=PR&PRODCODE=00000000&PRODLETT=K.

Ress, David; Heeger, David J.; "Neuronal correlates of perception in early visual cortex"; Nature Neuroscience; bearing dates of Mar. 10, 2003 and Apr. 2003; vol. 6., No. 4; pp. 414-420.

Schaeffel, F ; Wilhelm, H.; Zrenner, E.; "Inter-individual variability in the dynamics of natural accommodation in humans: relation to age and refractive errors"; The Journal of Physiology; bearing a date of 1993; pp. 1-3; Copyright 1993 by The Physiological Society:; printed on Jul. 13, 2004; located at: http://jp.physoc.org/cgi/content/abstract/461/1/301.

Starner, T; "Human- powered wearable computing"; Systems Journal; IBM Corporation; bearing various dates of 1996 and 1998; pp 1-14; printed on Jun. 1, 2004; located at: http://www.research.ibm.com/journal/sj/mit/sectione/starner.html.

U.S. Appl. No. 11/523,172, Goodall et al.
U.S. Appl. No. 11/495,167, Hillis et al.
U.S. Appl. No. 11/495,165, Hillis et al.
U.S. Appl. No. 11/494,803, Goodall et al.
U.S. Appl. No. 11/492,716, Hillis et al.
U.S. Appl. No. 11/004,713, Hillis et al.
U.S. Appl. No. 11/004,551, Goodall et al.
U.S. Appl. No. 11/004,533, Goodall et al.
U.S. Appl. No. 11/004,473, Hillis et al.

* cited by examiner

FIG.1
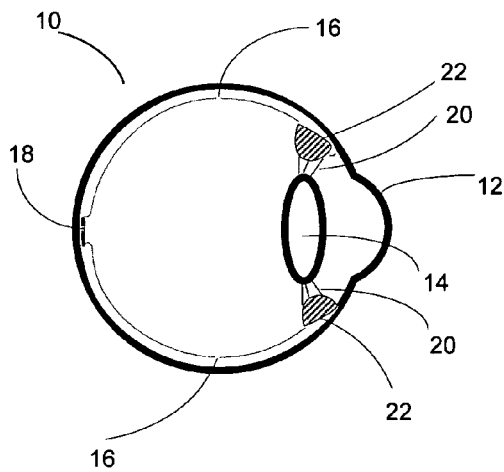
FIG. 1A
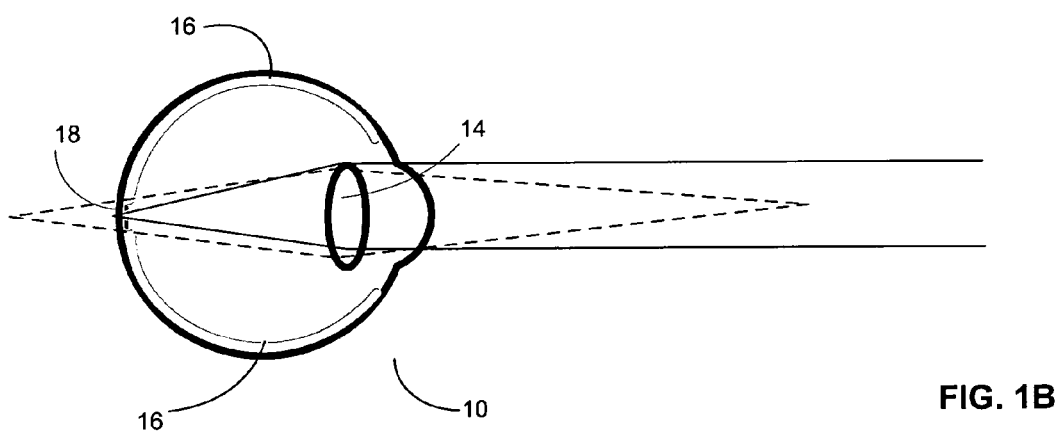
FIG. 1B
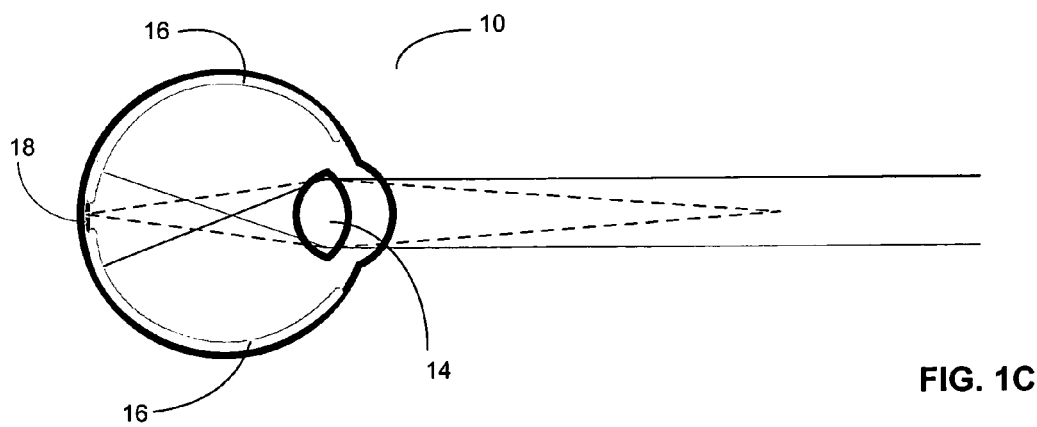
FIG. 1C

Contact Lens

Intraocular Lens

METHOD AND SYSTEM FOR ADAPTIVE VISION MODIFICATION

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s); the present application also claims the earliest available effective filing date(s) from, and also incorporates by reference in its entirety all subject matter of any and all sibling, parent, grandparent, great-grandparent, etc. applications of the following listed application(s):

1. U.S. patent application entitled TEMPORAL VISION MODIFICATION, naming W. Daniel Hillis, Roderick A. Hyde, Muriel Y. Ishikawa, Edward K. Y. Jung, Nathan P. Myhrvold, Clarence T. Tegreene and Lowell L. Wood, Jr. as inventors, filed substantially contemporaneously herewith, now U.S. Pat. No. 7,334,894.
2. U.S. patent application entitled VISION MODIFICATION WITH REFLECTED IMAGE, naming W. Daniel Hillis, Roderick A. Hyde, Muriel Y. Ishikawa, Edward K. Y. Jung, Nathan P. Myhrvold, Clarence T. Tegreene and Lowell L. Wood, Jr. as inventors, filed substantially contemporaneously herewith, now U.S. Pat. No. 7,350,919.
3. U.S. patent application entitled METHOD AND SYSTEM FOR VISION ENHANCEMENT, naming Eleanor V. Goodall, W. Daniel Hillis, Roderick A. Hyde, Muriel Y. Ishikawa, Edward K. Y. Jung, Nathan P. Myhrvold and Lowell L. Wood, Jr. as inventors, filed substantially contemporaneously herewith, now U.S. Pat. No. 7,334,892.
4. U.S. patent application entitled ADJUSTABLE LENS SYSTEM WITH NEURAL-BASED CONTROL, naming Eleanor V. Goodall, W. Daniel Hillis, Muriel Y. Ishikawa, Roderick A. Hyde, Edward K. Y. Jung, Nathan P. Myhrvold and Lowell L. Wood, Jr. as inventors, filed substantially contemporaneously herewith, now U.S. Pat. No. 7,344,244.

TECHNICAL FIELD

The present application relates, in general, to the field of optical systems for improving and enhancing vision.

BACKGROUND

The use of lenses for correcting vision problems produced by deficiencies in the optical system of the human eye has been known for many years. FIG. 1A illustrates, in schematic form, the anatomy of the human eye 10. Light enters eye 10 through cornea 12, passes through lens 14, and strikes retina 16, the light-detecting inner surface of the eye. The fovea 18 is a central region of retina 16 having particularly high acuity. Lens 14 is attached around its periphery to zonular fibers 20. Zonular fibers 20 are connected to ciliary body 22. Ciliary body 22 is a sphincter muscle which opens when it is relaxed, thereby generating tension in zonular fibers 20. Ciliary body 22 releases tension on zonular fibers 20 when it is contracted. Lens 14, because of its inherent elastic properties, tends to assume a rounded form when it is not subject to external forces. Thus, when ciliary body 22 contracts, lens 14 becomes more rounded, while relaxation of ciliary body 22 produces flattening of lens 14. Cornea 12 provides a significant portion of the refractive power of the optical train of the eye, but the capacity for accommodation is contributed by lens 14.

FIG. 1B illustrates a relaxed (unaccommodated) eye 10, in which lens 14 is flattened. As indicated by the solid lines in FIG. 1B, light from distant objects will be focused on retina 16 (and specifically, on fovea 18) by lens 14, but light from near objects (indicated by the dashed lines) will be focused behind the retina, and thus appear out of focus at the retina. FIG. 1C illustrates an accommodated eye 10, in which lens 14 has assumed a more rounded form. In the accommodated eye, light from near objects (indicated by dashed lines) is focused on retina 16 (fovea 18), while light from distant objects (indicated by solid lines) is focused in front of the retina, and thus is out of focus at retina 16.

In a normal, healthy eye, adjustment of lens 14 is sufficient to focus images on retina 16 within a wide range of distances between the visual target-object and the eye. Myopia (near-sightedness) and hypermetropia (far-sightedness) occur when images entering the eye are brought into focus in front or in back of the retina, respectively, rather than exactly on the retina. This is typically caused by the eyeball being too long or too short relative to the focal-adjustment range of the lens. Eyeglasses with spherical focusing lenses of the appropriate optical refractive power can be used to compensate for myopia or hypermetropia.

Another common and readily corrected visual problem is astigmatism, a focusing defect having orientation-dependence about the optical axis of the eye that may be corrected by interposition of a cylindrical lens having appropriate refractive power and axis-angle of orientation. Other visual focus problems exist as well (e.g., coma and other higher order optical aberrations), but are less readily characterized and more difficult to correct in a practical manner. In general, focal problems caused by irregularities in the dimensions of the cornea, lens, or eyeball can be corrected, providing the optical properties of the eye can be characterized and a suitable (set of) optical element(s) manufactured and then positioned relative to the eye.

Aging subjects may experience presbyopia, a decrease in the ability to focus on proximate visual targets caused by reduced flexibility of the eye lens relative to the tractive capabilities of the operative musculature attached thereto. Difficulty in focusing on such proximate visual targets can be alleviated with the use of 'reading glasses'. Subjects who require correction for myopia as well as presbyopia may use "bifocal" glasses having lens regions that provide correction for both 'near' and 'far' vision. The subject selects the type of correction by looking toward the visual target through the appropriate portion of the lens. Elaborations and extensions on such systems are now common, including "trifocal glasses" and "progressive glasses," the latter featuring a continuous gradation in optical properties across a portion of the eyeglass and thus of the visual field thereby regarded.

Adjustable optical systems are used in a wide variety of devices or instruments, including devices that enhance human vision beyond the physiological range, such as telescopes, binoculars, and microscopes, as well as a numerous devices for scientific and industrial applications independent of human vision, such as in test, measurement, control, and data transmission. Such devices typically make use of complex systems of multiple lenses and optical components that are moved with respect to each other to provide a desired level of focus and magnification. Adjustable lens systems that have been proposed for use in eyeglass-type vision enhancement include electroactive lenses, as described in U.S. Pat. Nos. 6,491,394 and 6,733,130 and various types of fluid lenses, as described in U.S. Pat. Nos. 4,466,706 and 6,542,309, as well as assorted multi lens systems (see e.g., U.S. Pat. Nos. 4,403, 840 and 4,429,959).

Various methods have been developed for measuring neural activity. Electrical measures of neural activity can be obtained from electrodes positioned within a neural structure to record activity from one or a few cells, or from electrodes placed on a skin surface to measure electrical fields, typically representing the activity of multiple cells. Magnetic fields generated by the nervous system can also be measured by devices such as SQUIDs (superconducting quantum interference devices), which may be placed on the scalp to measure magnetic fields from the brain. Other methods, such as magnetic resonance imaging and optical (spectroscopic) measurements permit neural activity to be determined indirectly by measuring correlates of brain activity such as blood flow or metabolic activity. Similarly, muscle activity can be assessed through measurement of electrical and magnetic fields generated by muscles (e.g., electromyographic measures or EMG), as well as by measurements of muscle force, displacement, or related parameters.

SUMMARY

A method and system for providing adaptive vision modification uses one or more adjustable lenses. Automatic, real-time lens adjustment may be used to correct the subject's near and far vision during routine activities or to provide vision enhancement beyond the physiological ranges of focal length or magnification, in support of specialized activities. Automatic lens adjustment may be based upon detection of neural or muscular activity correlated with the orientation or the state of focus of the eye. Various features of the present invention will be apparent from the following detailed description and associated drawings.

BRIEF DESCRIPTION OF THE FIGURES

The features of the present invention are set forth in the appended claims. The invention may best be understood by making reference to the following description taken in conjunction with the accompanying drawings. In the figures, like referenced numerals identify like elements.

FIG. 1A illustrates the anatomy of the eye;

FIG. 1B illustrates focusing of the normal eye for distance vision;

FIG. 1C illustrate focusing of the normal eye for near vision;

DETAILED DESCRIPTION

In the following detailed description, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context dictates otherwise. The meaning of "a", "an", and "the" include plural references. The meaning of "in" includes "in" and "on." A reference to the singular includes a reference to the plural unless otherwise stated or inconsistent with the disclosure herein. In particular, though reference is frequently made to "the eye" or "the lens", in most embodiments two lenses or lens systems will be used, one for each eye of the subject, and that, while the operation of the lenses will typically be the same, they will typically be adjusted separately to meet the individual needs of the two eyes.

Figure 2:
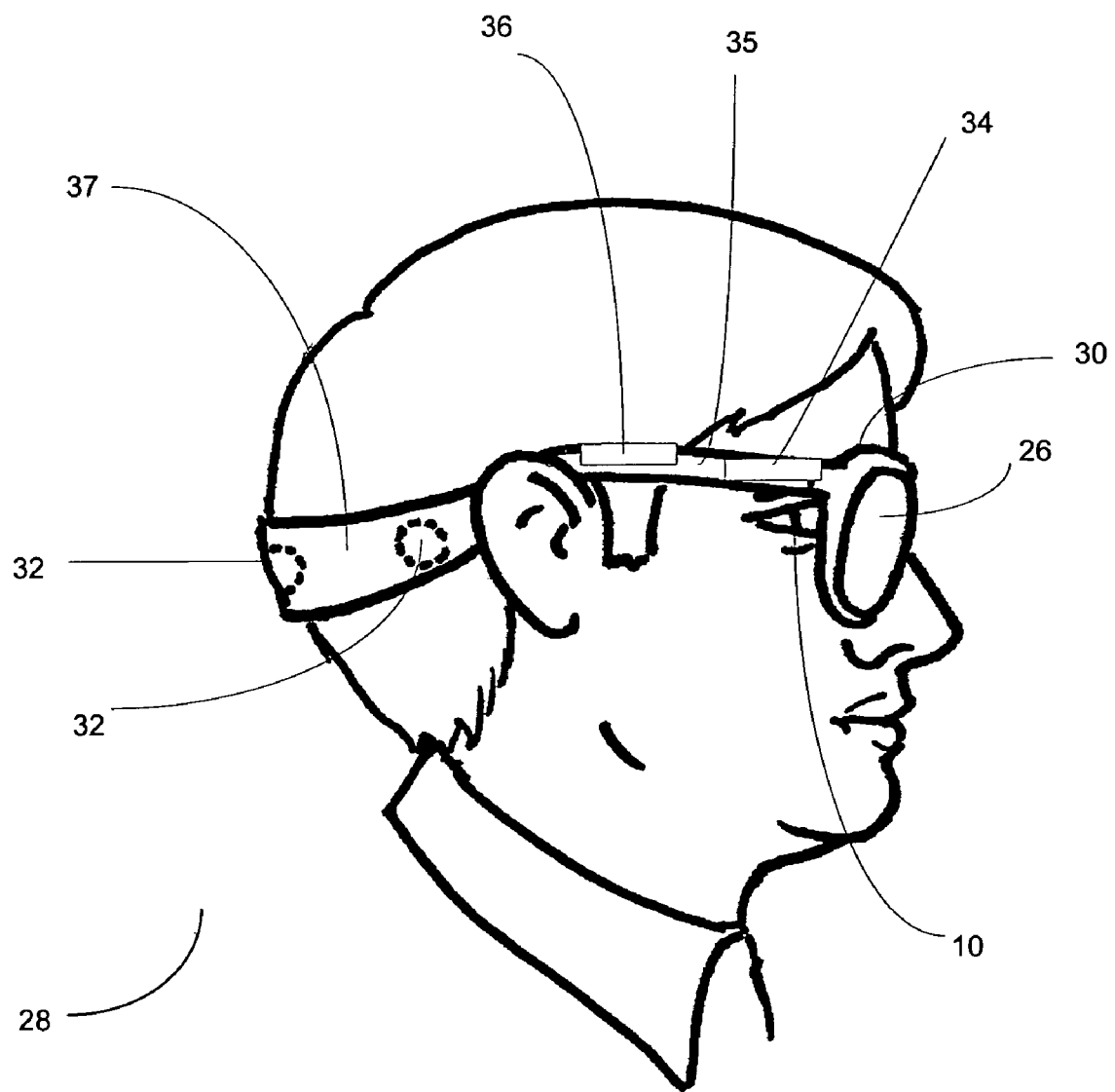
FIG. 2 illustrates an embodiment in which components are mounted in an eyeglass frame.

FIG. 2 illustrates an exemplary embodiment of a system for modifying the vision of a subject 28. Adjustable lens system 26 is positioned with respect to eye 10 of subject 28 with mounting 30, which in this example is an eyeglass frame. Sensors 32 detect neural activity from subject 28 which contains components correlating with the quality or focal condition of the visual input. Sensors 32 may be positioned with respect to the head of subject 28 by means of a wearable positioning means, which in this example is a headband 37 connected to bow 35 of eyeglass frame 30. Data from sensors 32 is routed to processor 34. Processor 34 processes the data and based upon the processed data generates a control signal that drives adjustable lens system 26 to provide a modified visual input to subject 28. Power supply 36, also mounted in bow 35 of mounting 30, provides power to adjustable lens system 26, sensor 32, and processor 34. Connections between various system components may be via conventional electrical cabling or wiring, or may be remote or wireless connections formed by RF or inductive couplings.

Figure 3:
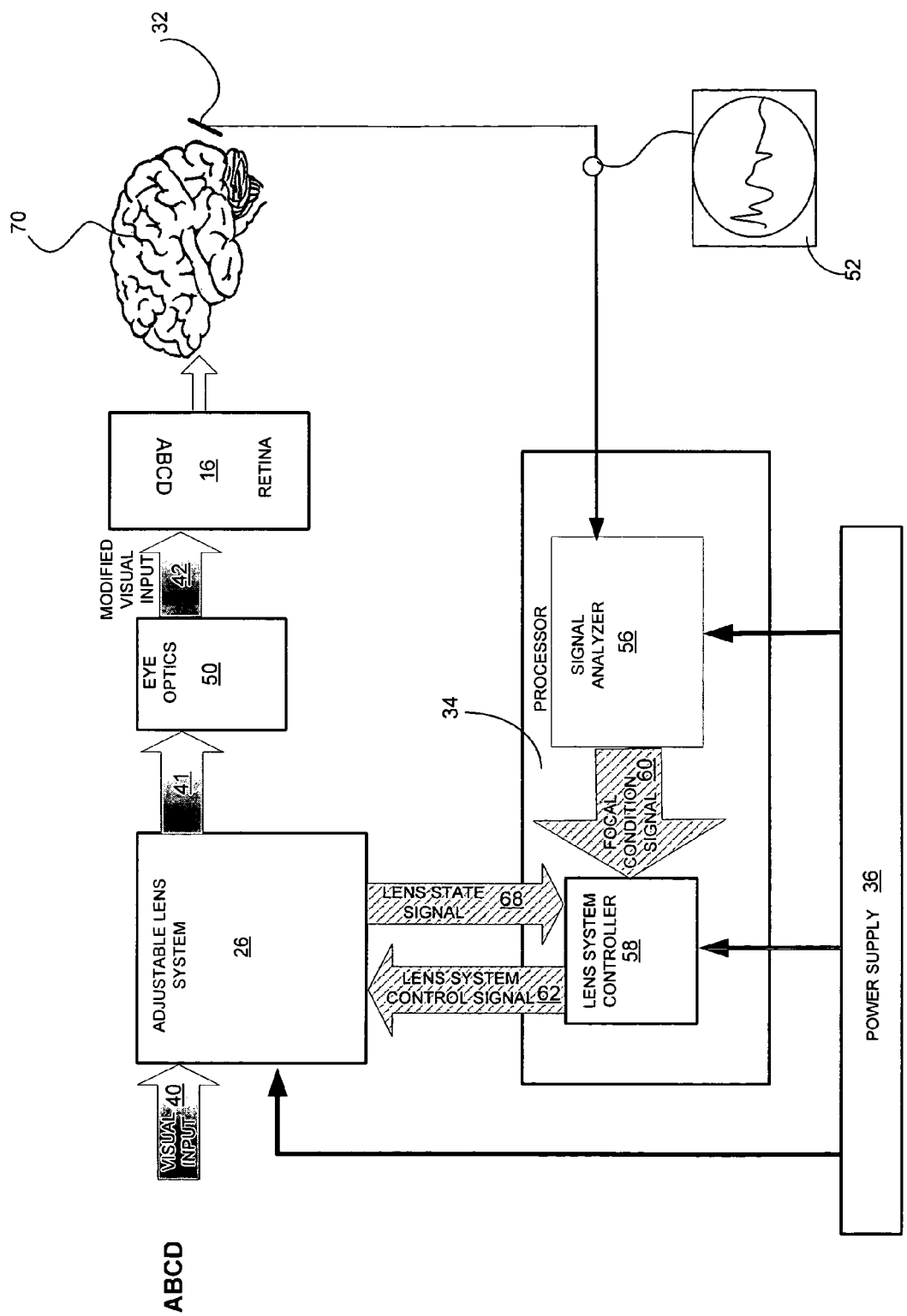
FIG. 3 is a schematic diagram of an embodiment of the invention as depicted in FIG. 2.

FIG. 3 is a schematic diagram of an exemplary embodiment, illustrating the functional relationships of various system components. A visual input 40 passes through adjustable lens system 26 and eye optics 50, and strikes retina 16, where it is detected (as modified visual input 42) by photoreceptors in the retina 16 of the eye. A neural signal is generated that travels through the optic pathways of brain 70. The optic pathways may include, but are not limited to, the retina, optic nerve, lateral geniculate nucleus, superior colliculus, and visual cortex. Neural activity may be detected from various regions of the brain, particularly from optic pathways of the brain but also from other cortical areas. Neural activity is detected by one or more sensors 32 and routed to processor 34 as neural signal 52. Processor 34 includes signal analyzer 56 and lens system controller 58. Processor 34 may include various combinations of analog or digital electronic circuitry, discrete components or integrated circuits, and/or hardware, software, or firmware under computer or microprocessor control, including optical analog devices. Processor 34 may include a variety of functional and/or structural components for supporting the function of signal analyzer 56 and lens system controller 58, such as memory, timing, and data transmission structures and devices. Neural signal 52 is processed by signal analyzer 56 to obtain information relating to the focal condition of the image on retina 16. A focal condition signal 60 reflecting the quality of the retinal image as determined from neural signal 52 is generated by signal analyzer 56 and sent to lens system controller 58. Lens system controller 58 generates lens system control signal 62, which is sent to adjustable lens system system 26. Lens system controller 58 may also receive as input a lens state signal 68 from adjustable lens system 26, which provides information regarding the state of adjustable lens system 26. Lens state information may be used in computations performed by one or both of signal analyzer 56 and lens system controller 58. Adjustable lens system 26, sensor 32, and processor 34 and its components, signal analyzer 56 and lens system controller 58, may all be powered by power supply 36. Alternatively, certain components may have separate power sources. The invention is not limited to any particular power supply configuration.

Figure 4:
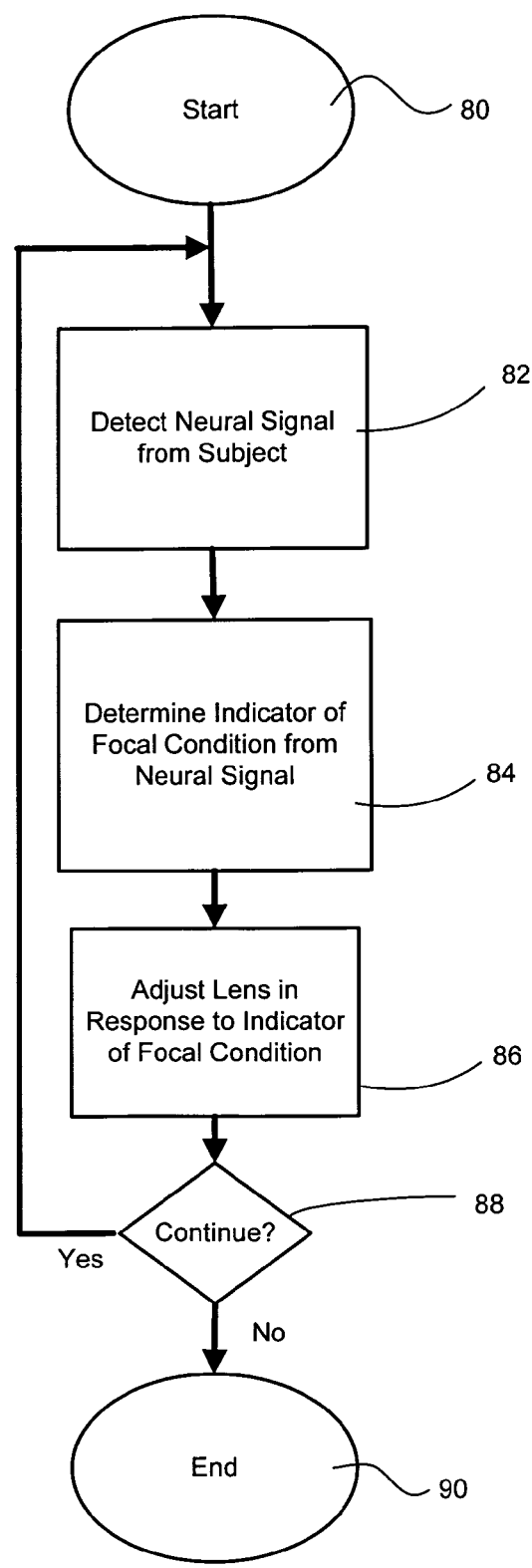
FIG. 4 is a flow diagram of the operation of the embodiment of FIG. 3.

FIG. 4 is a process flow diagram for a method of enhancing the vision of a subject, as may be carried with a system as depicted in FIG. 3. In step 82, a neural signal is detected from a subject. Subsequently, in step 84, an indicator of focal condition is detected from the neural signal. The indicator of focal condition correlates with state of focus of a real-time visual input to the subject. In step 86, a lens system is adjusted responsive to the indicator of focal condition. In order to provide ongoing visual enhancement to the subject, after step 86, process control returns to step 82, and the process is repeated as long a visual enhancement is desired.

Figure 5:
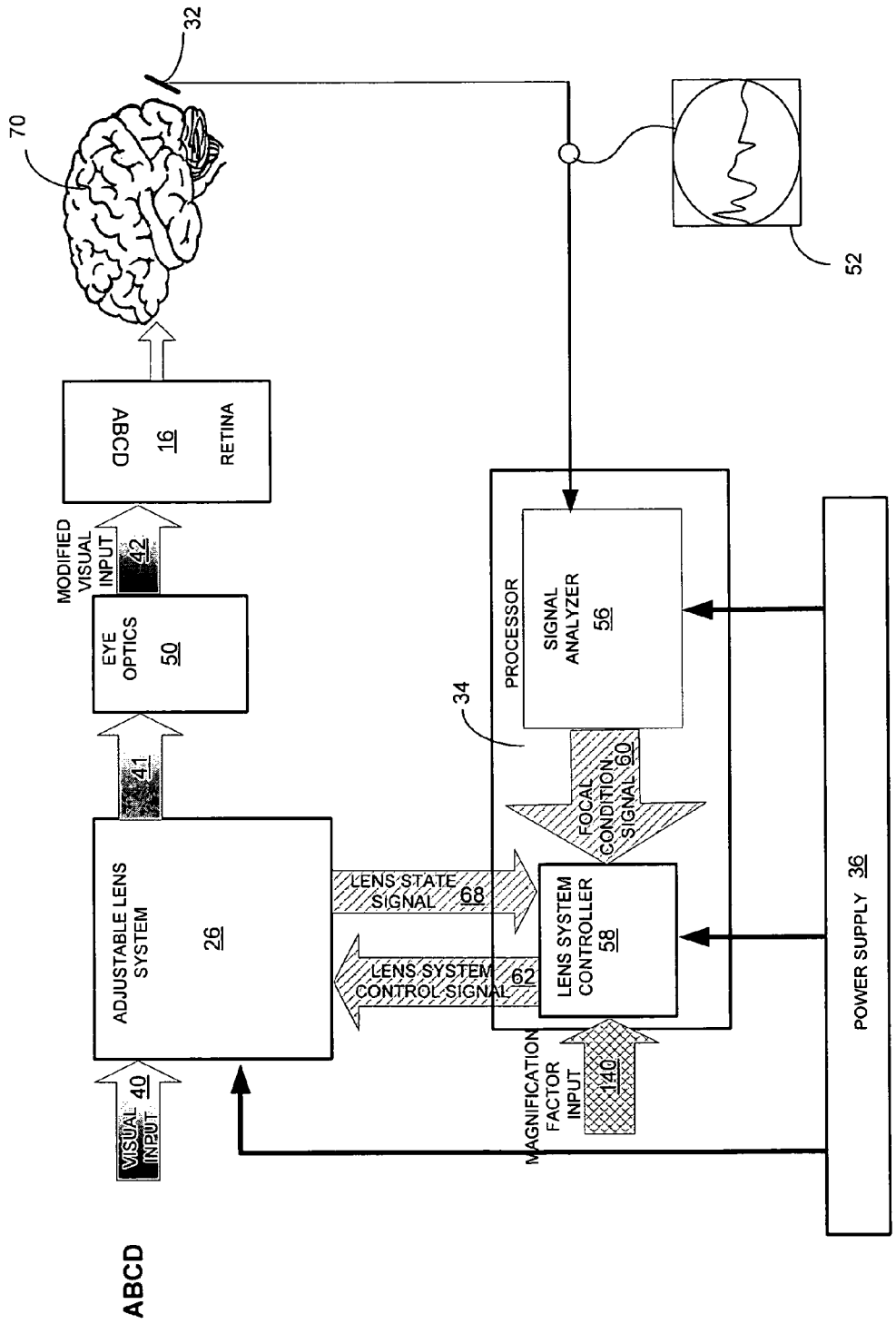
FIG. 5 illustrates an alternative embodiment.

FIG. 5 is a schematic diagram of a further embodiment suited for certain specialized applications requiring image magnification outside the physiological range of human vision. As illustrated in FIG. 3, visual input 40 passes through adjustable lens system 26 and eye optics 50, and strikes retina 16 as modified visual input 42, where it is detected by photoreceptors in the retina of the eye. Neural activity is detected by one or more sensors 32 and routed to processor 34 as neural signal 52. Neural activity may be detected from various regions of brain 70. Processor 34 includes signal analyzer 56, which processes 52 to generate focal condition signal 60, and lens system controller 58, which generates lens system control signal 62 responsive to focal condition signal 60. Neural signal 52 is processed by signal analyzer 56 to obtain information relating to the focal condition of the retinal image. A focal condition signal 60 reflecting the quality of the retinal image is generated by signal analyzer 56 and sent to lens system controller 58.

Processor 34 is generally as described above in connection with FIG. 3. However, processor 34 is adapted to also receive a magnification factor input 140, and generation of lens system control signal 62 is based upon magnification factor input 140 as well as focal condition signal 60. Magnification factor input 140 may be entered into processor 34 by various methods; it may be preprogrammed at a fixed value or entered by the subject. It is contemplated that the magnification factor will be used for special applications (e.g., close-up detail work or viewing distant objects) and that the subject may prefer to adjust the magnification to meet the requirements of a particular application. Manual selection of the magnification factor may be accomplished, for example, by configuring the device with one or more preprogrammed magnification factor values, and having the subject press a button on the eyeglass frame to cycle through magnification values until arriving at the desired magnification value; clearly provision also may be made for continuously-variable magnification control. Alternatively, a desired degree of magnification may be derived by the control processor 34 based upon some portion of the neural input 52. As described previously, lens system control signal 62 is sent to adjustable lens system 26. Lens system controller 58 may also receive as input a lens state signal 68 from adjustable lens system 26, which provides information regarding the state of adjustable lens system 26. Lens state information may be used in computations performed by one or both of signal analyzer 56 and lens system controller 58. Adjustable lens system 26, sensor 32, and processor 34 and its components, signal analyzer 56 and lens system controller 58, may all be powered by power supply 36, or alternatively, certain components may have separate power sources.

Figure 6:
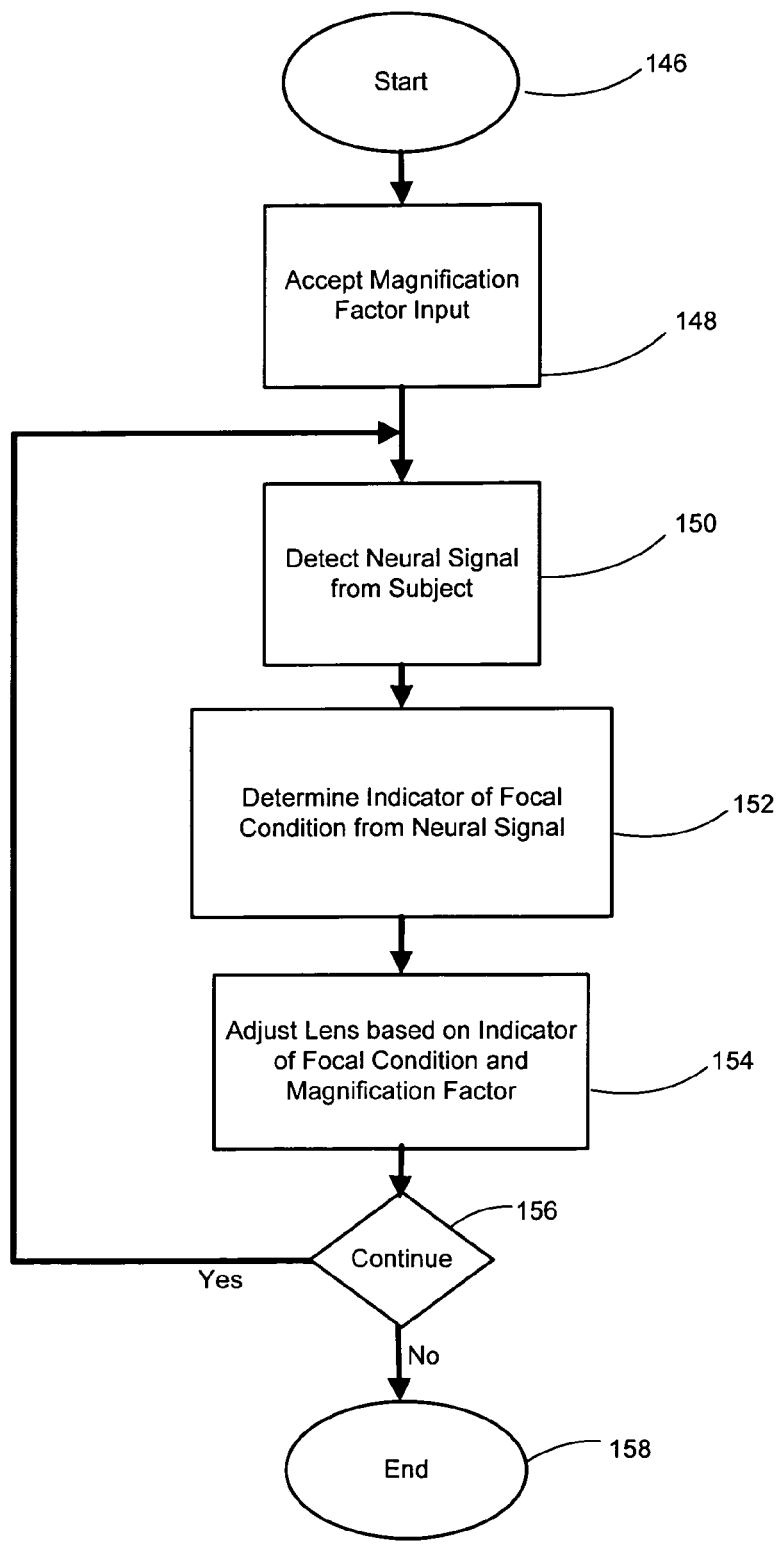
FIG. 6 is a flow diagram of the operation of the embodiment of FIG. 5.

The method of operation of the embodiment of the system shown in FIG. 5 is depicted in the flow diagram of FIG. 6. At step 148, a desired magnification factor input is accepted, which may be accomplished by various means, as described above. At step 150, a neural signal is detected from the subject. At step 152, an indicator of focal condition is determined from the neural signal, and at step 154, the lens system is adjusted based upon the indicator of focal condition and the magnification factor. In order to provide ongoing vision modification, at step 156 process control is returned to step 150, and steps 150 through 154 are repeated for as long as vision enhancement at the selected magnification is desired. Note that the process depicted in FIG. 6 may be part of a larger process, and that by including additional control loops, it would be a simple matter to provide for the input of an updated desired magnification factor value, during an ongoing control process.

As illustrated by the foregoing examples, the various embodiments may comprise a number of basic components, the structure and operation of which will now be described in greater detail. These components may include an adjustable lens system 26, which, as represented in FIG. 3, one or more sensors for detecting a neural or neuromuscular signal (e.g., sensor 32, as shown in FIGS. 3 and 5); processor 34, which includes a signal analyzer 56 and lens system controller 58; and power supply 36.

Various types of adjustable lens systems may be used in practice, and the invention is not limited to any particular type of adjustable lens system or set thereof, these two terms being used synonymously herein. However, certain adjustable lens systems may be more suitable than others, with small size, low weight, rapid adjustment, and compatibility with other system components being considerations for some applications. Depending on the particular intended application, certain considerations may be of greater importance than others, and thus the best choice of lens system will vary from application to application. While in some cases a single lens may be preferable due to smaller size and lighter weight, the term "adjustable lens", as used herein, refers to adjustable lenses and lens systems, including combinations of one or more lenses as well as other optical elements, which may include reflectors, refractive elements, beam splitters, active or passive filters, and so forth.

Conventional eyeglass lenses and contact lenses are typically characterized by their spherical lens strength or optical power (expressed in positive or negative diopters, the reciprocal of their focal length measured in meters-distance), cylindrical lens strength, and cylindrical axis orientation. Lenses may modulate the spatial frequency content of an image formed thereby (e.g., by adjusting the focus of the image) and may also modulate the light intensity of the image as a function of wavelength, e.g., by spectrally-dispersive properties of their bulk composition or coatings applied to their surfaces. Suitable adjustable lenses or lens systems may be characterized by these and additional focus or image-quality parameters. Lens systems may be used to provide image magnification outside the physiological range of human vision, and hence may be characterized by a magnification strength factor as well. An adjustable lens system used to provide vision correction may preferably permit the adjustment of each of these parameters, although in particular applications and for particular subjects, not all of these parameters may need to be adjusted. Independent adjustment of each of the various parameters may be desirable in some cases, but in many cases may not be required.

A number of designs for fluid-based adjustable lenses have been proposed which may be suitable for use. Fluid lenses utilize one or more fluids having appropriately selected indices of refraction. One approach is to enclose fluid within a deformable shell, and to increase fluid volume or pressure to deform the shell and thus change the optical strength of the lens, as disclosed in U.S. Pat. Nos. 4,466,706, 5,182,585, 5,684,637, 6,069,742, 6,542,309 and 6,715,876, which are incorporated herein by reference. Another approach is to utilize two immiscible liquids of differing refractive properties contained within a chamber, and modify the shape of the fluid-fluid interface in order to change the optical strength of the lens. The surface tension properties of the interior of a chamber are modified, for example, through an applied voltage (and thus electric field and gradients thereof) to adjust the shape of the fluid-fluid interface. Such fluid lenses, as disclosed in U.S. Pat. No. 6,369,954, which is incorporated herein by reference in its entirety, may also be suitable for use in some applications.

Another suitable type of adjustable lens or lens system may be an electro-active lens as described in U.S. Pat. Nos. 4,300,818, 6,491,394 and 6,733,130, also incorporated herein by reference. These lenses include one or more layers of liquid crystal or polymer gel having refractive power that may be modulated, e.g., electrically. An advantage of this type of lens is the refractive power can be adjusted selectively in different regions of the lens, making it possible to produce nearly any desired lens, including a lens that compensates for higher order optical aberrations, or a lens having regions with different focal strengths (comparable to a bi-focal or tri-focal lens), such that all or a portion of the lens can be adjusted. It is also possible to construct a lens system that can be rapidly switched from one focal length to another with the use of this technology.

In some embodiments, an adjustable lens system may be made up of multiple lenses or other optical elements, and adjustment may be accomplished by moving one optical element with respect to another or with respect to the subject. Such movements may include one or all of changing the distance, angle-of-orientation, or off-axis displacement between two or more optical elements. The adjustable lens system may include a lens mechanism and a lens actuator that is used for actuating the lens mechanism. Thus, the lens mechanism itself may not receive control signals directly from the lens system controller. A lens mechanism and lens actuator may be formed integrally, or they may be separate elements depending on the design of the lens system.

Adjustable lens systems may modify incident light in some specified manner. Adjustable lenses may bend (refract) incident light rays; they may also filter the incident light to modify the spectral composition of the incident light or to change the imaged intensity at one or more selected spectral wavelengths or wavebands. An adjustable lens system may have an adjustable transmissivity (or transmittivity), which adjustment may be wavelength-dependent. In a broad sense, an optical element may be any device or system that receives an input image and produces an output image that is a modified version of the input image; thus in certain embodiments the modified image is not formed entirely or even in significant part of incident light that has been transmitted through the lens system, but partly or mostly (including entirely) of light that has been generated by the lens structure to form a new image. In some embodiments, the term 'optical element' or 'optical system' may encompass systems including cameras and displays. Such an optical element may modulate the incident image in ways not possible with lenses that transmit incident light; e.g., the optical element may transform the incident image by shifting the spectral content or the intensity of some or all wavelengths relative to the incident light corresponding to the image. Adjusting the optical element may include adjusting one or more focal lengths, adjusting one or more cylindrical corrections, adjusting one or more distances of an optical element relative to an eye of the subject, adjusting the orientation-angle of the optical element with respect to the optical axis of the eye, adjusting the off-axis displacement of one or more optical elements relative to the optical axis of the eye, or adjusting the pan-or-tilt of one or more optical elements relative to the optical axis of the eye.

In one embodiment, the method may be considered to be a method of modifying a view of the environment. The method includes steps of detecting a neural signal from a subject, extracting information relating to an image condition of at least a portion of the view of the visual environment from the neural signal, determining a modification to the view based upon information relating to the image condition, and adjusting an optical system to produce modification of the view. The optical system may include, but is not limited to, optical components such as lenses, reflectors, refractive elements, active and passive optical filtering systems including optical attenuators and amplifiers, and beam splitters such as may be used for modifying incident light. In some embodiments, rather than modifying transmitted light, the optical system may detect and process an incident image and generate a modified version of all or part of the incident image.

As depicted in FIGS. 3 and 5, an indicator of focal condition may be determined from a neural signal detected from the subject. Neural activity can be recorded from the brain or other regions of the nervous system using a variety of measurement techniques well known to those of skill in the art, including electrical, magnetic, and optical measurements techniques. Electrical recordings can be made using electrodes implanted within the brain or surface electrodes placed on the scalp or on the surface of the brain. Electrodes may be placed on the skin, e.g., near the eye, to detect electrical potentials from the retina, as described in U.S. Pat. No. 4,255,023, incorporated herein by reference in its entirety. Implanted electrodes are capable of recording activity from one or a small number of nerve fibers or cell bodies. See, for example, the methods and devices described in U.S. Pat. No. 6,647,296, incorporated herein by reference in its entirety. Electrodes on the scalp or brain surface record from a large number of neurons in aggregation, providing information about the aggregate activity of large populations of neurons, as described in exemplary U.S. Pat. Nos. 5,052,401, 6,647,296, and 6,690,959, which are incorporated herein by reference in their entirety.

Magnetic recording techniques can be used as an alternative to electrical recording techniques (see, e.g. U.S. Pat. No. 6,066,084, and Heeger, D. J. and Ress, P., Nature Reviews Neuroscience, vol. 3, pp. 142-151, February 2002, both of which are incorporated herein by reference in their entirety). Superconducting quantum interference devices or SQUIDs are among the types of magnetic field-sensing systems that can be used to record neural activity, as described in U.S. Pat. Nos. 5,309,095 and 6,195,576, incorporated herein by reference in their entirety. Other techniques for measuring neural activity include optical, electrooptical or optoelectronic techniques such as optical coherence tomography and near IR imaging. Measurements of absorption and scattering of visible or IR light may provide an indication of neural activity, as described in U.S. Pat. Nos. 5,187,672, 5,792,051, 5,853,370, 5,995,857, and 6,397,099, all of which are incorporated herein by reference in their entirety. Neural signals may be recorded by various methods as described herein, by other methods as are known in the art or may be developed, and are not limited to any particular methods.

In some embodiments, a sensor may be adapted for detecting a neuromuscular signal from the subject. The term neuromuscular signal, as used herein, refers to a signal detected from either a nerve or a muscle that relates to the activation of, or intention to activate, a muscle. Thus, in some cases, the neuromuscular signal may be detected from the nervous system of the subject, including central nervous structures (including, but not limited to motor cortex) as well as peripheral nerves innervating muscles. In other cases, the neuromuscular signal is detected directly from a muscle. In the case that the neuromuscular signal is detected from the central or peripheral nervous system, neural recording techniques as have been described previously may be used. Note that the measurement of electrical and magnetic signals from peripheral nerves is well established and a variety of techniques for measuring such activity are known to those of skill in the art. Optical techniques as discussed previously may also be adapted for making peripheral measurements. Methods for measuring electrical or magnetic signals from muscles are well known, and include sensors implanted within a muscle, positioned on the exterior of a muscle, or positioned near, on or under a skin surface near the muscle(s) of interest. The neuromuscular signal may be an electromyelographic or EMG signal. Such signals may be recorded for example, from an extraocular muscle, a ciliary muscle, the iris, or a facial muscle of the subject. As used herein, "neuromuscular signal" may also refer to a measure of muscle force, displacement, pressure, volume or related parameters detected with suitable transducers located in, on, or adjacent a muscle (including, but not limited to, positions near, on or under the skin surface) in order to measure muscle mechanical activity or its correlates.

Neural signals may be detected by various methods, and the signal processing and analysis will depend on the type of neural signal and the method of detection. The term "neural signal", as used herein, refers not only to signals that are direct measures of neural activity, but also to signals that are correlated with neural activity. These may include, but are not limited to, measurements of electrical or magnetic fields generated by nerve cells, axons, processes, or fibers; measurements of metabolic activity in nerve cells or supporting cells such as glial cells; or measurements of blood flow in selected brain regions, as determined by optical, biochemical, thermal, or other measurements. Neural activity may be the activity of individual cells, small numbers of cells or populations of cells, including activity measured from cell bodies or cellular processes such as axons, dendritic trees, or nerve fibers, in one or more regions of the central or peripheral nervous system.

Muscular activity refers to activity detected from muscles, including but not limited to electric, magnetic or electromagnetic fields corresponding to muscle activation, motion, position, relaxation or contraction. As with neural activity, muscular activity may also be measured indirectly through measurement of blood flow, temperature, or metabolic activity; force or displacement may also be measured, as may various other parameters as known or may be discovered by those of ordinary skill in the art.

The terms signal and signals may be used interchangeably herein, and may refer to activity originating from one or more sources detected with the use of one or more sensors, unless the context dictates otherwise.

Neural and neuromuscular signals suitable for providing feedback information in the various embodiments described herein, and other embodiments, may be recorded from a variety of neural structures, including but not limited to the cerebral cortex, especially the occipital region thereof, the retina, optic nerve, lateral geniculate nucleas, superior colliculus, and other portions of the optic pathway, motor nerves innervating muscles of the eyes (especially the ciliary muscles, extraocular muscles, and iris) and surrounding regions (e.g., certain facial muscles).

If implanted electrodes or other sensors are used, the sensor(s) may be implanted within the selected location according to methods described in the references incorporated above. Detected signals may be transmitted from one or more sensors to other system components by RF or inductive coupling, including but not limited to transponder-type sensing and signal-transceiving.

In some embodiments, sensors may be positioned on the head of the subject. In such embodiments it may be desirable to make use of a wearable positioning device to position or orient the sensor(s) with respect to the head of the subject. FIG. 2, for example, illustrates an embodiment in which several sensors 32 are positioned with respect to the head of subject 28 through the use of a headband 37, which is affixed to bows 35 of an eyeglass frame. As depicted in FIG. 2, headband 37 contains a single row of sensors 32. The width of headband 37 may be adjusted to hold larger numbers of sensors, arranged in an array of multiple rows, or in any configuration deemed useful or convenient. Because headband 37 generally overlays regions of the cerebral cortex devoted to visual processing, sensors positioned by means of headband 27 may be well suited for detecting activity from visual processing areas of the cortex. Sensors may also be mounted in or on bow 35, or other portions of the eyeglass frame.

Figure 7:
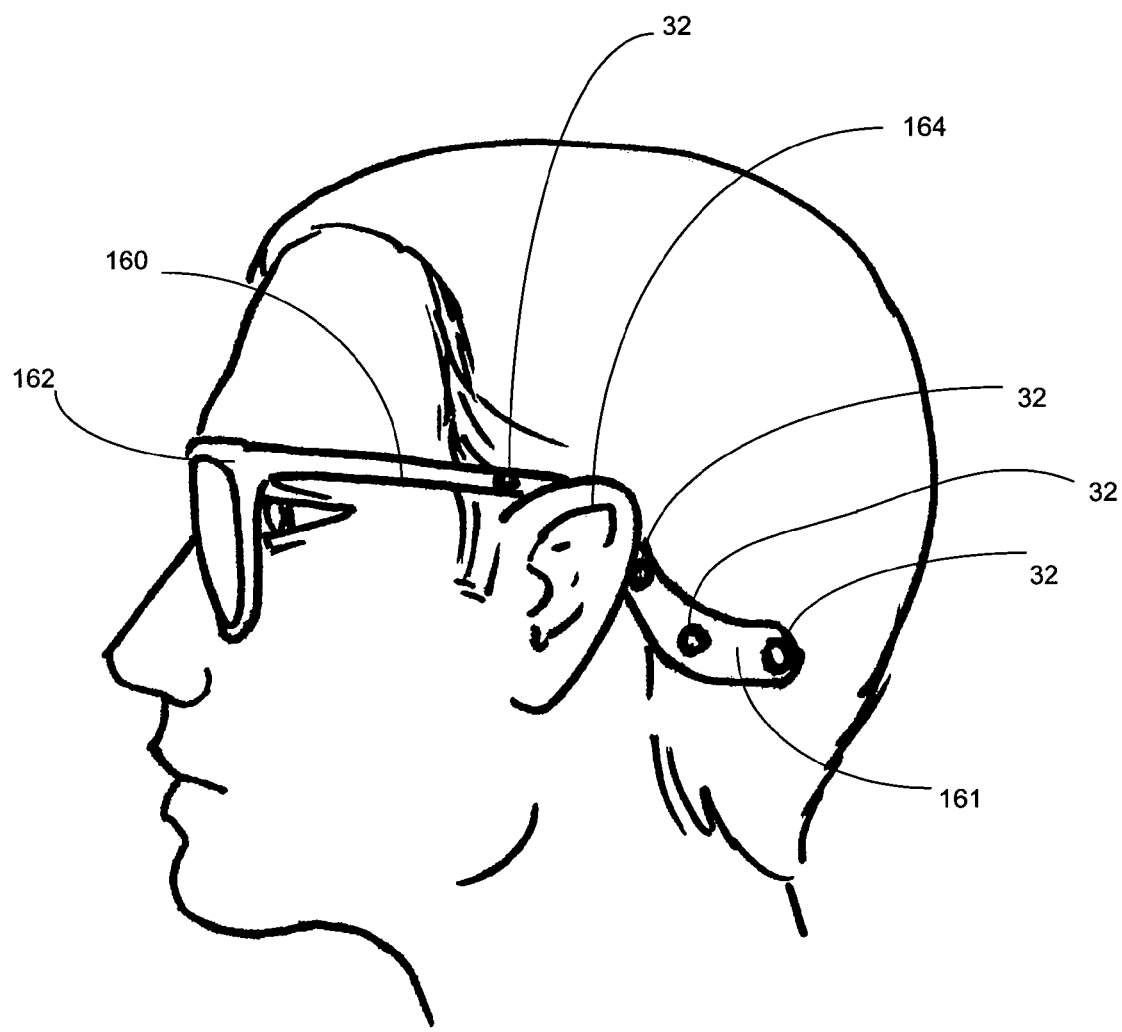
FIG. 7 depicts an alternative method of positioning sensors.

FIG. 7 illustrates a further embodiment of a wearable positioning device in which one or more sensors 32 are mounted in specialized bow 160 of an eyeglass frame 162 (which also functions as mounting 30, as depicted in FIG. 2). Specialized bow 160 may include a rear extension 161 shaped to extend backwards or downwards of the ear 164 and fit closely about a portion of the occipital region of the head.

Wearable positioning devices of various types may be devised, and the invention is not limited to any particular type of wearable positioning device. Wearable positioning devices may include hats, headbands, and helmets, or other head coverings, apparel or adornments, as are known or may be devised by those of skill in the relevant art. Exemplary versions of such devices are described in U.S. Pat. Nos. 4,709, 702, 5,323,777, and 6,397,099, incorporated herein by reference in their entirety. Depending on the type of sensors used, the wearable positioning device may be close-fitting or relatively loose; for example, some types of EEG electrodes may need to be pressed tightly against the scalp of a subject, while magnetic or optical signals may be detected without close physical contact between the sensor and the skin being required. Various methods may be devised for positioning sensors with respect to the head of a subject, and the invention is not limited to any particular sensor position or type of sensor.

Figure 8:
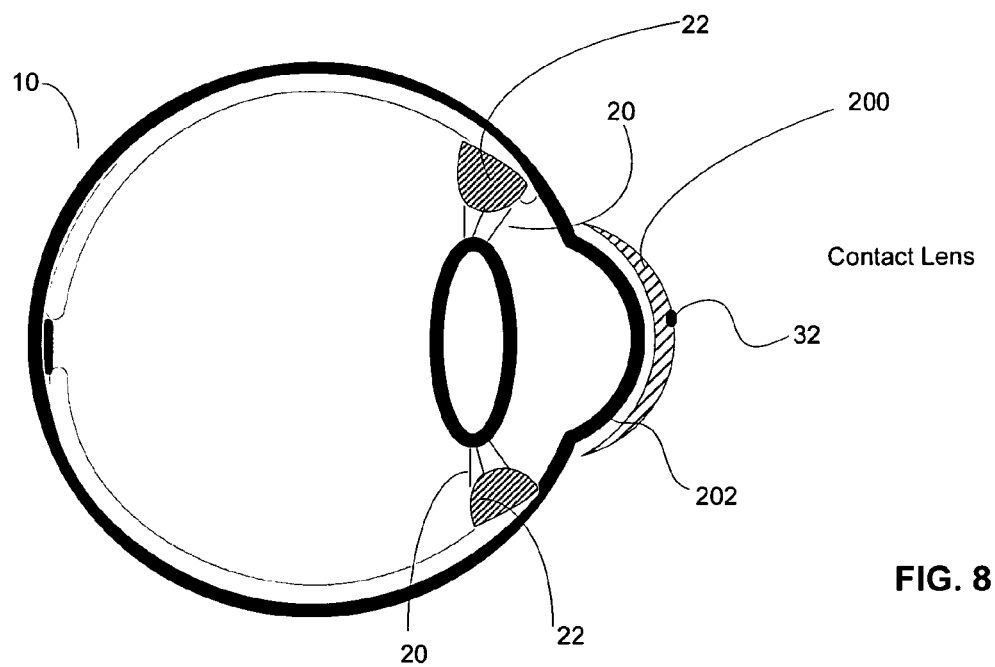
FIG. 8 is an embodiment including a contact lens system.

In a further alternative embodiment, illustrated in FIG. 8, the adjustable lens system is constructed in form of a contact lens 200 that is worn on the cornea 202 of eye 10. Other components of the system may be mounted on or manufactured integrally with contact lens 200, or they may be packaged separately at a remote location and power and data signals transmitted to the contact lens 200 inductively or via other suitable mechanisms. The term 'remote location', as used herein, refers to any location not in direct physical contact with contact lens 200, including positions relatively close to the contact lens on the body of the subject, more distant locations on the body of the subject, or locations separated from and at a distance from the body of the subject.

Figure 9:
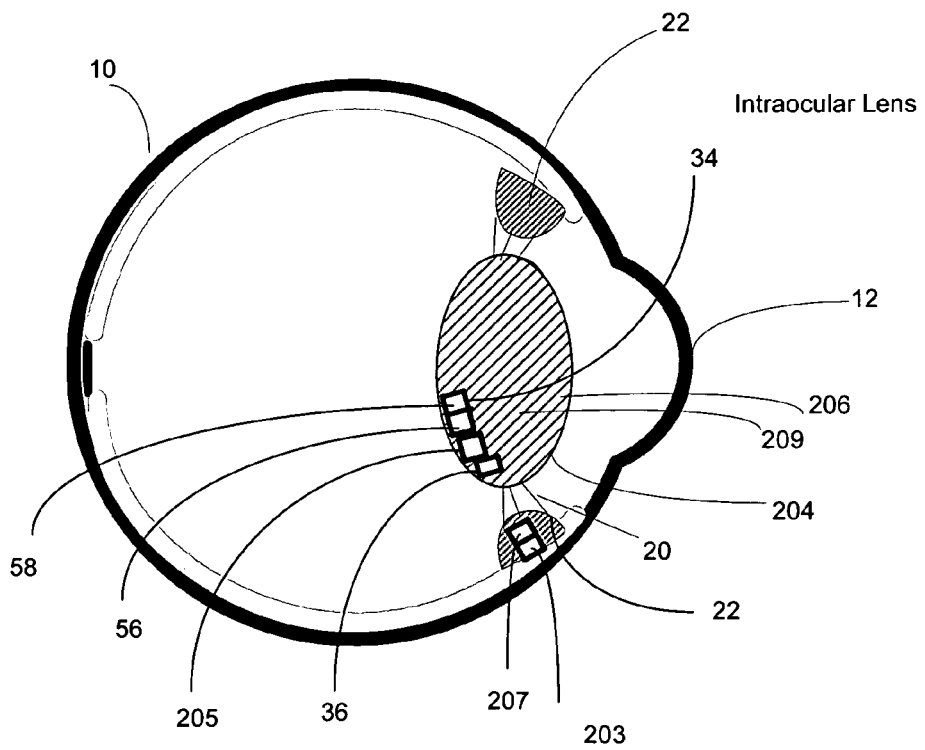
FIG. 9 is an embodiment including an intraocular lens.

Some embodiments of the systems and devices described herein may also be configured as an intraocular lens device 206, as depicted in FIG. 9. In embodiments in which the system or device is implemented as an intraocular lens system, it is anticipated that typically the natural lens will have been removed and an adjustable intraocular lens device 206 implanted within the eye (e.g., within lens capsule 204) as illustrated in FIG. 9. Various adjustable intraocular lens designs may be used in this embodiment, as exemplified by U.S. Pat. Nos. 4,373,218, 4,564,267, 4,601,545, 4,787,903, and 5,108,429, all of which are incorporated herein by reference in their entirety. The eye optics will then include the cornea. However, in some cases the intraocular lens may be implanted either in front of or behind the natural lens, so that the eye optics may include the natural lens as well as the cornea. The intraocular version is not restricted to use with any particular combination of eye optics, though the correction provided by the lens optics will typically take into account the degree of focus provided by the eye optics.

In the exemplary embodiment of FIG. 9, neuromuscular activity is detected from a sensor 203 in ciliary muscle 22, which neuromuscular activity may correlate with effort to adjust the focus of the eye. Intraocular lens device 206 may include processor 34, which may be a microdevice attached to or formed integrally or otherwise associated with adjustable lens system 209. Processor 34 and sensor 203 include transceivers 205 and 207, respectively, to permit the transmission of data and power signals between the two devices. A neuromuscular signal detected by sensor 203 may thus be transmitted to a signal analyzer 56 in processor 34. As in other, previously described embodiments, lens system controller 58 generates a lens control signal to drive actuation of adjustable lens system 209. Adjustable lens system 209 and processor 34 and controller 58 may be powered by power supply 36. Sensor 203 may be powered remotely by power supply 36, or, alternatively, may include a separate power supply. In additional variants of this embodiment, one or more sensors may be positioned in, on or proximate to intraocular lens device 206 for detecting neuromuscular signals from ciliary muscles or retina. In still other variants, sensors for detecting neural or neuromuscular signals may be placed in other locations in or on the body of the subject, the locations being selected appropriately for detecting specific neural or neuromuscular signals, and detected signals transmitted to processor 34. Processor 34 need not be located at intraocular lens device 206. Instead, processor 34 may be located at the sensor, or at some other location, and signals transmitted wirelessly between the sensor, processor, and adjustable lens. Operation of embodiments configured as an intraocular device, as illustrated in FIG. 9, is substantially the same as that of other, previously described embodiments, for example, as illustrated in the flow diagram of FIGS. 4 or 6.

As illustrated in FIG. 3, the main functional components of processor 34 are signal analyzer 56 and lens system controller 58. Processor 34 may include various combinations of analog or digital logic circuitry in the form of discrete components or integrated circuits, hardware, software, and/or firmware under computer or microprocessor control. Processor 34 may also include various functional and/or structural components such as memory, timing, and data processing, transmission and reception structures and devices necessary to support the operation of signal analyzer 56 and lens system controller 58. It will be recognized by one skilled in the art that the functions and operation of Processor 34 may be implemented in software, in firmware, in special purpose digital logic, or any combination thereof, and that the design of processor 34 to perform the image analysis and lens system control tasks described below may be performed in various ways by a practitioner of ordinary skill in the relevant art. Digital signal processing (DSP) chips or devices suitable for signal processing are commercially available or may be designed for specific applications. Processor 34 may be implemented in specialized hardware (e.g. as an Application Specific Integrated Circuit or ASIC) to minimize size and weight of the system while maximizing speed of operation. Alternatively, some portions of processor 34 may be implemented in software running on a microprocessor-based system. This will provide greater flexibility, relative to specialized hardware, but system size and weight generally will be increased. Although processor 34 (including signal analyzer 56 and lens system controller 58) may be packaged as a single unit, in some cases it may be preferable to package certain components separately. For example, as discussed previously, processor 34 may include a receiver for receiving an image-characterization signal transmitted from a detector and a transmitter for transmitting control signals to the adjustable lens system.

In some embodiments, the processor may include a signal input adapted to receive a time-varying visual focal condition signal detected from the body of the subject, a pre-processor configured to pre-process the visual focal condition signal to generate a pre-processed signal, and a signal analyzer configured to determine at least one visual image quality parameter from the pre-processed signal, which will be sent to a lens system controller which generates as output a lens system control signal for driving the adjustable lens system. The pre-processor may perform various functions, including filtering, amplification, artifact removal, clutter removal, and noise reduction, as are known in the art of signal processing.

Signal analyzer 56 may include appropriately configured digital circuitry, hardware, and/or a microprocessor running suitable software. Tasks performed by the neural signal analyzer may include a variety of manipulations of one or more neural signals, including pre-processing steps such as detection of the relevant portions of the detected neural signal, processing to increase the signal-to-noise ratio, and analysis of the neural signal to determine values of selected image quality metrics. While the full range of neural signal processing tasks may be performed by the neural signal analyzer in some embodiments, in other embodiments, selected pre-processing steps may be performed by appropriately configured neural signal detector(s). Appropriate selection of sensor configuration may be used to improve signal quality. For example, by using multiple sensors it may be possible to perform signal averaging, to subtract out common noise components from signal, or to perform multivariate analysis of signals. Such approaches are known to those skilled in the art of acquisition and processing of biological signals. The type of signal processing approach selected may depend on the specific signals detected. Signal processing methods for use with electrical and magnetic neural signals have been described, as exemplified by U.S. Pat. Nos. 4,844,086, 4,974, 602 5,020,538, 5,655,534, 6,014,582, 6,256,531, 6,370,414, 6,544,170, and 6,697,660, all of which are incorporated herein by reference in their entirety.

Preliminary signal processing to improve the signal to noise ratio or otherwise make the detected signal easier or more convenient to work with may include a variety of conventional signal processing techniques, such as filtering, signal averaging, adjusting offset and scaling, removal of clutter and artifacts, such techniques being known to those with skill in the art.

After preliminary signal processing steps have been completed, the processed signal is analyzed to obtain one or more measures of visual focal condition. The term "visual focal condition" as used herein, means any of various parameters, also referred to as "quality parameters" or "indicators of focal condition", which may be determined or derived from a detected neural or neuromuscular signal and used to characterize the visual input at the retina of the subject, particularly with regard to meaningful or useful content. The term "quality" is not intended to imply "good quality" or "high quality" but rather quality in general, whether good, bad or mediocre. "Quality parameters", "indicators of focal condition", or "focal conditions", may be determined from components of a neural or neuromuscular signal that correlate with the quality of the visual input. Components or groups of components of a neural or neuromuscular signal that correlate with a focal condition or quality of a visual input may be referred to as "visual focus-related events", and may include, for example, a peak or series of peaks of neural or muscular activity (or indirect indicators of activity such as metabolism or blood flow) in a signal recorded from a neural or neuromuscular structure.

Image sharpness, or fineness-of-focus (i.e. sharpness or 'crispness' of focus of the retinal image, indexed by a relative large fraction of high spatial wavenumber image-pattern on the retinal foveal region) is an important measure of image quality. Sharpness or fineness-of-focus (or lack thereof) in the retinal image will be reflected in the activation of photoreceptors in the retina and in the neural signals transmitted through various portions of the visual pathways. Image focus may be broken down into a number of components thereof, such as spherical focus or cylindrical focus (with an associated axis of orientation). Choice of quality metric in certain embodiments may be matched to the attribute(s) of optical aberrations that can be corrected by the adjustable lens system or optical system. In some cases, detecting (and subsequently correcting) only one focal attribute may be performed. In other cases, multiple focal attributes may be detected and subsequently corrected.

Image sharpness or fineness-of-focus is not the only measure of image quality. Depending on the intended application of the system, other image attributes or quality metrics may be considered of greater interest or importance. These may include metrics such as for, example, image contrast or intensity or spectral content.

The neural or neuromuscular signal is analyzed to determine an indicator of the focal condition of the imaged visual input. Various components of the detected neural or neuromuscular activity may correlate with the quality or state of focus of the image of a visual input. A neural response may be produced in response to a visual input, the focal condition of the imaged visual input, or an in-focus or out-of-focus state of the imaged visual input. A component of a neural or neuromuscular signal that correlates with the quality or focal condition of an imaged visual input may be referred to as a visual focus-related event. Quality or focal condition may refer to one or multiple parameters of focus, e.g., spherical focus, cylindrical focus, cylindrical axis, intensity or sharpness of the image, etc. The neural response may be conscious or unconscious, i.e., the subject may or may not be consciously aware of the neural response. Providing that the response may be measured, it is not necessary that the subject be consciously aware of it. It is contemplated that components of neural activity will correlate with the focal state of the visual input in various ways. For example, some components of neural activity may correlate with the detection of an in-focus imaged visual input. Other components of neural activity may correlate with the detection of an out-of-focus imaged visual input. Still other components of neural activity may correlate with the intention of the subject to focus his or her eyes on the visual input. Alternatively, components of neural activity may correlate with effort on the part of the subject to focus his or her eyes on the visual input or move his or her eyes (and specifically, the optic axis of the eyes) toward a particular visual target. The non-real-time analysis of EEG signals for identifying various parameters of visual focus, under controlled visual input conditions, has been demonstrated (see U.S. Pat. No. 5,052,401, incorporated herein by reference).

In some embodiments, the quality parameter may include a time or amplitude measure of a neural signal component that correlates with the perception by the subject of an in-focus state of the imaged visual input. In other embodiments, the quality parameter may include a time or amplitude measure of a neural signal component that correlates with the perception by the subject of an out-of-focus state of said imaged visual input. In some out-of-focus states, the neural signal component may correlate with the perception by the subject of an imaged visual input focused in front of the retina of the eye, while in others it may correlate with the perception of a visual input focused behind the retina of the eye. The quality parameter may include a time or amplitude measure of a neural signal component that correlates with an effort by the subject to focus at least one eye on at least portion of the visual input or alternatively, with effort by the subject to direct the optical axis of at least one eye toward at least a portion of the targeted visual input. Various time and amplitude measures of a peak of a detected neural signal may be used as one or more quality parameters. In other aspects, the neural signal may be converted to the frequency domain and the amplitude of one or more frequency components may be used as quality parameters.

An amplitude measure of a neural signal component may be the amplitude of a maximum or minimum measured with respect to a selected baseline level, or an amplitude difference measure (i.e., the distance between selected maxima or minima). A time measure may be a latency or duration of a maximum or a minimum, the width of a peak, or any other temporal feature of a portion or component of the neural signal. The time measure may be the time between occurrences of any selected features or events in the neural or neuromuscular signal, or duration of a specified sequence of features or events.

Neural or muscular activity may correlate with the subject's efforts (either conscious or unconscious) to correct the focus of the visual input, for example, by adjusting the lens of the eye (by contraction or relaxation of the ciliary muscle), by adjusting the pupil (by contraction or relaxation of the iris), or by adjusting facial muscles (squinting) to modify the focal length of the eye. Neural or muscular activity that correlates with actual, attempted, or planned eye movements directed toward bringing an imaged visual target into position on the fovea by moving the optic axis of at least one eye toward a chosen visual target, including tracking and vergence movements (i.e., convergence or divergence), may provide information useful for controlling the focal condition of the imaged visual input, as well. Neural activity may be generated in the central nervous system that correlates with muscle activation but occurs prior to actual muscle activation.

In some embodiments, particular patterns of neuromuscular activity are associated with particular focal states of the imaged visual input, so that detected neuromuscular activity serves as a source of feedback control for adjusting a lens system. For a given subject, it is expected that certain patterns of neuromuscular activity will correlate with certain visual focal conditions in a consistent and predictable manner, at least over the short term. However, for a given subject, the correlation may drift over time in some cases. This may be due to various causes, ranging from changes in the recording setup (e.g., shift in position of sensors) to adaptation of the subject to the modified visual input. It is expected that neuromuscular activity that correlates with a particular focus state will be similar from subject to subject; nevertheless, it may be the case that there will be enough subject-to-subject variability that the system may need to be calibrated for each subject. Therefore, calibration may be performed prior to routine use of the device according to various embodiments disclosed herein. Furthermore, it may be necessary to calibrate the system from time to time during use, to compensate for drift, as discussed above, or for temporal changes in the subject's visual system. Calibration sessions may be held at regular intervals or only when needed, as indicated by decreasing system performance. Some embodiments may be configured to perform calibration on an on-going basis.

System calibration may be carried out through the use of a training protocol during which the subject is presented with well-defined visual inputs and the neural or neuromuscular activity patterns associated with various states of focus of the imaged visual input are determined. Such a training protocol may be patterned after the methods described in U.S. Pat. Nos. 4,953,968, 4,697,598, and 5,052,401, incorporated herein by reference in their entirety. In general, a series of visual inputs may be presented in which the focus of an imaged visual input is varied and the neural or neuromuscular activity produced in response to the visual inputs is measured.

In some embodiments, a predetermined relationship between quality of visual input and neural signal may be established by a training protocol that includes a steps of delivering a series of well-defined visual input having different values of the quality to the subject, detecting a series of neural signals produced in response to the series of well-defined visual inputs, and determining the quality parameter of the series of neural signals. In some embodiments, the training protocol may be performed prior to the use of the system. In other embodiments, the training protocol may be performed at intervals during the use of the system. The predetermined relationship may be stored in the form of series of data representing corresponding values of visual input and focal condition or quality parameters, or the predetermined relationship may be modeled as a mathematical equation or function so that the visual input may be calculated as a function of one or more focal condition or quality parameters determined from the detected neural or neuromuscular signal(s), and vice versa.

The system may include a lens system controller configured to receive one or more quality parameters as input and generate a lens system control signal for providing closed loop control of the adjustable lens system, as a function of the quality parameter(s). The lens system controller may be configured to generate a lens system control signal based upon a predetermined relationship between the value of at least one quality parameter and a modified visual input, as discussed above. The predetermined relationship may be defined by stored quality parameter values and stored corresponding visual input values. Alternatively, the predetermined relationship may be defined by a mathematical model that defines at least one quality parameter as a function of visual input. The lens system controller may be configured to generate a lens system control signal for updating the setting of the adjustable lens system at a specified update great. The lens system controller may include a device that includes a microprocessor, in which case the update rate may be controlled by a timer circuit or by a software loop, or by other methods known to those of skill in the relevant art. In still other embodiments, the update rate may be under hardware or firmware control. The lens system controller may be a closed loop controller that is adapted to control the adjustable lens system in substantially real-time.

Figure 10:
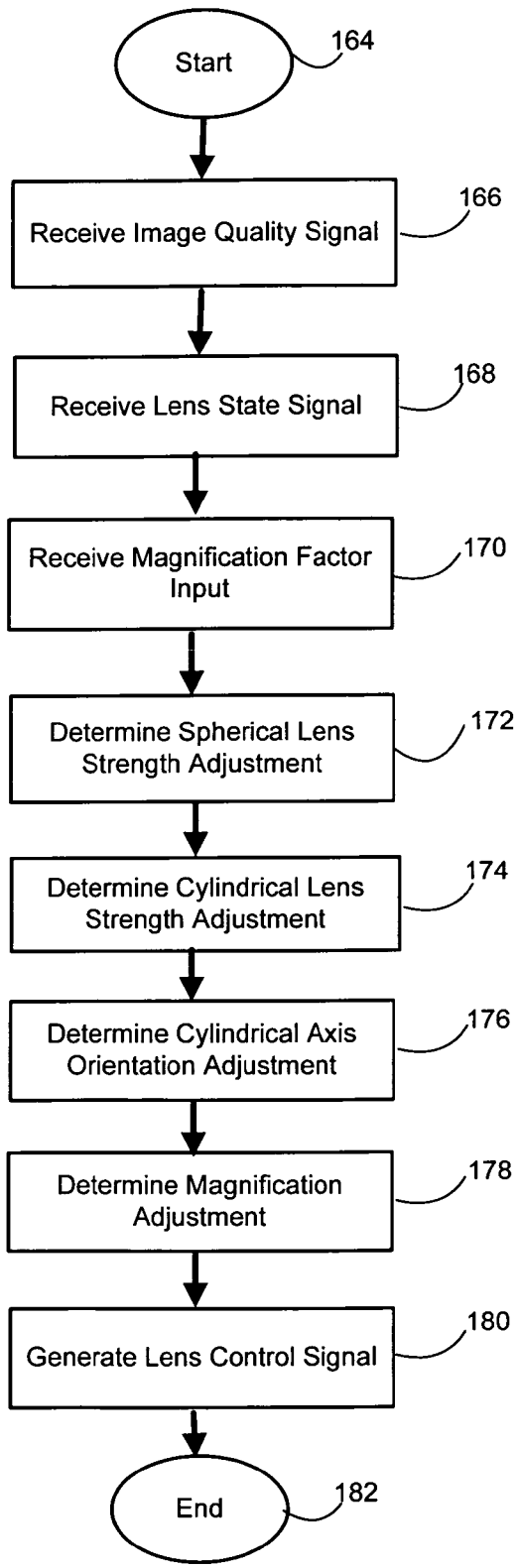
FIG. 10 is a flow diagram illustrating lens system adjustment.

FIG. 10 breaks down into greater detail the lens system control process as it may be performed by lens system controller 58 (in other words, the process performed at step 86 in FIG. 4 and step 154 in FIG. 6). At step 166, processor 34 receives focal condition signal 60. At step 168, processor 34 receives lens state signal 68. At step 170, processor 34 receives magnification factor input 140, which may be a stored value. Steps 166, 168, and 170 may be performed in any desired order; moreover, in some applications certain of the received parameters may not be adjusted, so the parameter value may be a stored constant value, or a particular step (e.g., the step of receiving a magnification factor value) may be omitted entirely. Subsequently, processor 34 (specifically lens system controller 58) determines a spherical lens strength adjustment at step 172, determines a cylindrical lens strength adjustment at step 174, determines a cylindrical axis orientation adjustment at step 176, and determines a magnification adjustment at step 178. Steps 172, 174, and 176 may be performed in other orders than depicted in FIG. 10; if one or more of the parameters are not adjusted, one or more of steps 172, 174, and 176 may be omitted as appropriate. Other steps not explicitly noted here but discussed above also may be included, e.g., determination of adjustments of lens system spectral transmissivity, so as to affect the overall brightness and/or relative spectral content of the light processed through the thereby-adjusted lens system. At step 180, lens system controller 58 generates a lens system control signal based upon the adjustments determined in steps 172, 174, and 176. Depending on the nature of the adjustable lens system and lens actuator, the control signal may reflect newly determined absolute settings for the adjustable lens system, or the control signal may reflect changes to lens system settings relative to the current lens system settings. Adjustable lens system settings may be adjusted to modify various indicators of focal condition in the neural or neuromuscular signal. Modification of the adjustable lens system settings may be selected to move one or more indicators of focal condition toward a specific target value, in a desired direction, or simply to produce a change in the image metric or quality attribute which may be used as a reference value in an adaptive control algorithm.

Determination of lens system adjustment may be performed by the using well-known principles of control system design. For example, an exemplary method for adjusting a lens system in response to the focal condition of visual input may include determining an adjustment direction in response to the indicator of focal condition and then adjusting the lens system in the determined adjustment direction. Determining the adjustment direction may include determining a change in the value of the indicator of focal condition caused by adjusting the lens system in the determined adjustment direction, by determining the value of the indicator of focal condition in the neural response produced by a previous instance of the visual input, and determining further change to the lens system adjustment based on the result of the previous adjustment. For example, if the previous adjustment produced a neural response correlating to a reduction in focal quality of the imaged visual input, the direction of lens system adjustment may be reversed. Conversely, if the adjustment produced a neural response correlating with increased focal quality of the imaged visual input, the next adjustment step may be in the same direction. Various lens system parameters (spherical focus, cylindrical focus, etc.) may be adjusted independently, and the determination of adjustment of each lens system parameter may be responsive to different indicators of focal condition. In some embodiments, a component of a neural signal indicating quality of a selected retinal region of the imaged visual field (e.g., the foveal region) may be measured and a lens system adjustment selected to optimize the foveal image applied to the entire lens, thus modifying the focal quality of the image over the entire retina. In other embodiments, the focus may be adjusted separately for areas of the adjustable lens system projecting onto different regions of the retina. These and other approaches for controlling lens system adjustments may be performed by an appropriately configured or programmed lens system controller, and may involve the controlled use of a lens system having other than purely spherical or cylindrical focusing capabilities.

In some embodiments, the controller may be configured to control an image modulator (which may be an adjustable lens system or other optical element or optical system) to cause a specified change in an indicator of focal condition. The controller may be configured to perform a comparison of the indicator of focal condition with a reference focal condition value and then to control the image modulator to decrease the difference between the indicator of focal condition and a reference focal condition value. In some cases it may be desired to increase the difference between the indicator of focal condition and a reference focal condition value. Parameters modified by the image modulator may include (but are not limited to) the focal length of the input image, the magnification of the input image, the cylindrical correction of the input image, or the radiant intensity of the input image.

The lens system controller may control a variety of lens system or optical system parameters, including any or all of transmissivity of the lens system over one or more spectral wavebands, intensity of light generated by an optical system, effective aperture of one or more components of the adjustable lens system or optical system, transverse position of at least one optical element relative to the optical axis of the eye, or one or more chromatic aberration correcting features of the adjustable lens system.

Timing is an important consideration in the operation of the present invention. In order to provide ongoing adaptive visual modification, correction or enhancement, the system updates the setting of the adjustable lens system in real-time or near-real-time. Moreover, in order to provide true adaptive vision correction, the focus of the adjustable lens system is adjusted to compensate for the current state of the eye optics and for the current visual input, without a priori knowledge of the visual input. In some cases this may be accomplished by completing a full update cycle (such as the process control loops depicted in FIGS. 4 and 6) in an amount of time less than or equal to the intrinsic accommodation time-response of lens of eye. The intrinsic accommodation time of the lens of the eye (i.e., that amount of time that it takes for the lens to adjust to a change in the distance to a visual target) is from about 2 to about 3 seconds for a large change in focal distance, and varies from subject to subject. Accommodation rates and accommodation distance-ranges vary as functions of age and health, being higher for children and lower for older adults. By adjusting the lens system faster than the intrinsic accommodation time, the lens-actuating musculature of the eye will be minimally worked, thus reducing eye strain and/or fatigue of eye muscles.

In some use-cases, it may be desirable to update the setting of the adjustable lens system at a rate that is as fast, or faster, than the visual pigment reversal rate of photoreceptors of eye. In particular, in some applications it may be desirable to update the lens setting at a rate faster than the visual pigment reversal rate of the photoreceptors having the fastest visual pigment reversal rate in the eye. In some embodiments, a controller is configured to provide closed loop control of the adjustable lens system on an ongoing basis. In some embodiments, the lens system controller is configured to adjust the adjustable lens system at a rate faster than the intrinsic accommodation time of the lens of the eye. In other embodiments, the lens system controller is configured to adjust the adjustable lens system at a rate faster than the visual pigment reversal rate of the photoreceptors of the eye.

It is thought that lens system adjustment update rates of at least about once every three seconds (⅓ Hz) may improve usefulness in general applications, and that update rates of about 1 Hz will be preferable for general applications. In higher-performance applications, update rates of about 3 Hz may be desirable, e.g. to minimize work that must be performed by the ciliary musculature of the eye's own lens. Update rates higher than 10 Hz may not provide additional benefit in some applications, due to the speed limitations inherent in other parts of the human visual system, though in some applications, this may not be the case. Thus, it is thought that update rates in the range of about ⅓ to about 10 Hz will be useful in practice, and that update rates in the range of about 1 to about 10 Hz will be more preferred, and that rates in the range of about 1 to about 3 Hz will be most preferred.

Timing of the update rate for lens system adjustment may be controlled in a number of ways. For example, each update cycle may be initialized by a signal from a timer chip or system clock; a software loop with an approximately-fixed cycle time may also control the timing. The design of systems using these and other timing control methods are well-known to those of skill in the art.

In some cases, in order to provide for rapid adjustment between one lens system setting and at least one other, rather than utilizing a single adjustable lens system and modifying the setting of that lens system, two or more adjustable lens systems or optical subsystems may be used, and suitable optics used to switch between the two or more lens systems. In the exemplary case of two lens systems, one useful application of this embodiment is to adjust the first and second optical subsystems to provide correction for near and far vision, respectively. Thus, switching between the two optical subsystems, the subject would obtain correction similar to what is currently provided by bi-focal lenses, but in an automated and potentially high-speed fashion.

Figure 11:
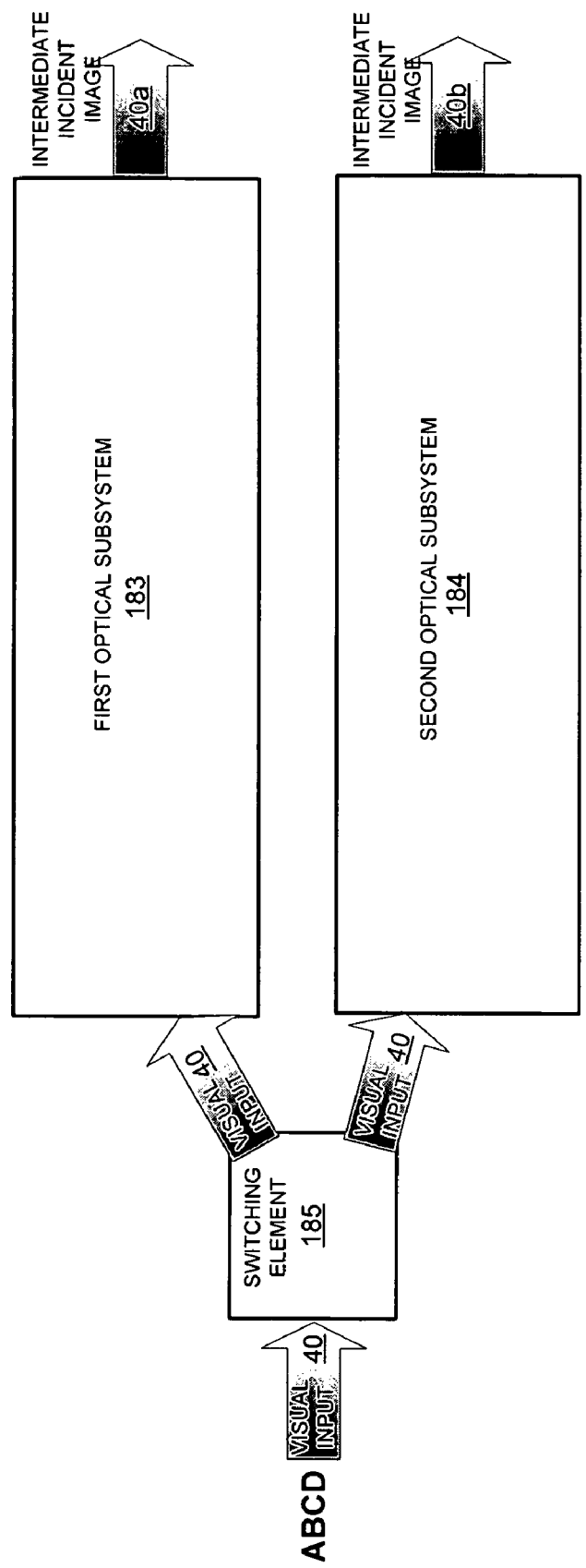
FIG. 11 illustrates an embodiment having two parallel optical paths.
Figure 12:
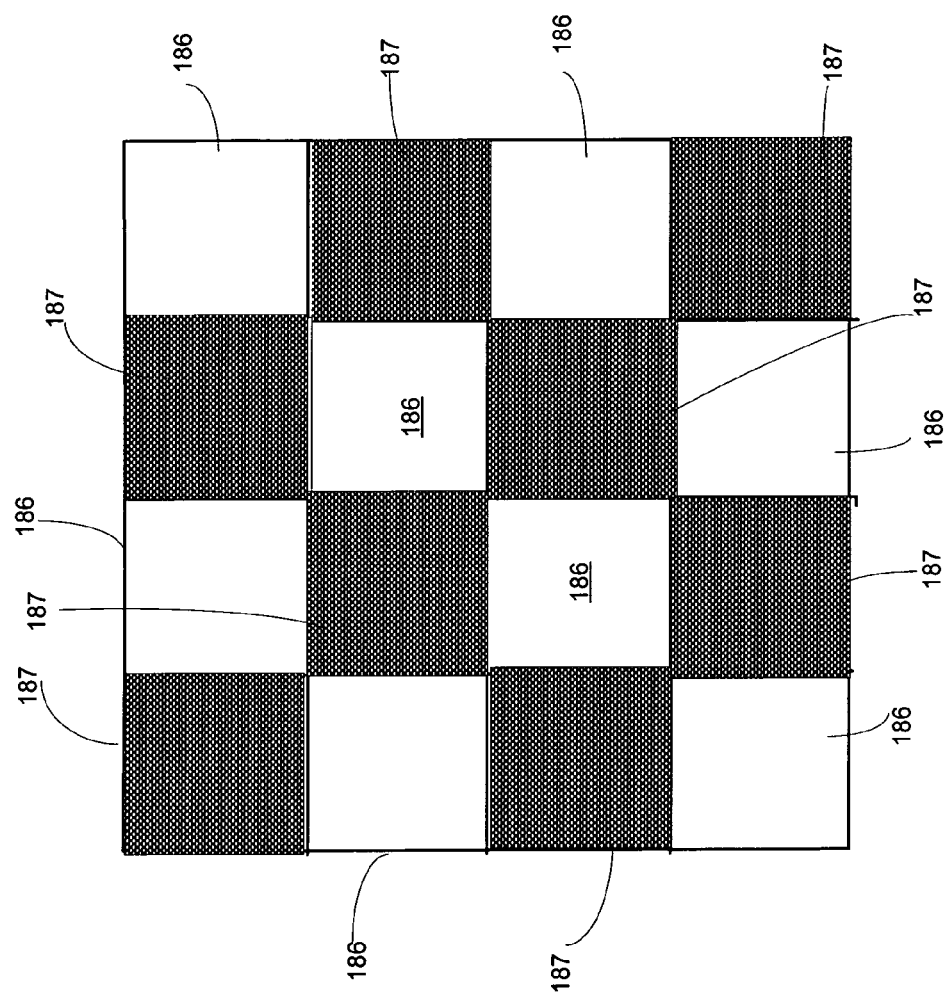
FIG. 12 illustrates the construction of an adjustable lens system having two parallel optical subsystems.

This approach is depicted schematically in FIG. 11. First optical subsystem 183 and second optical subsystem 184 have optical properties (e.g. spherical focal length, cylindrical focal power, and axis of orientation) that can be adjusted independently. First optical subsystem 183 and second optical subsystem 184 are set up in parallel between a visual input 40 and the eye of the subject. Visual input 40 may be switched rapidly between optical subsystem 183 and optical subsystem 184 by switching element 185, which may be an adjustable reflector or refractive element, such as a lens. Each of optical subsystem 183 and optical subsystem 184 may be an adjustable lens or lens system, controlled by a lens system controller as described previously. After passing through either optical subsystem 183 or optical subsystem 184, an intermediate incident image 40a or 40b, respectively, will be delivered to the eye of the subject. The optical system as depicted in FIG. 11 may be used in connection with lens control mechanisms as described previously herein. Another method for providing rapid switching between optical subsystem having different settings is to provide two or more optical subsystems having transmissivities controllable between substantially complete transmissivity and substantially zero transmissivity, such that the amount of light that is transmitted through each subsystem can be controlled. Parallel segments are maintained in the optical path between the eye and the visual target; by adjusting first and second-or-more controllable transmissivities appropriately, it is possible to switch rapidly between first and second-or-more segments. Parallel optical subsystems of this type may be constructed in the form of an electroactive lens system in which individually controllable lens areas are interleaved, as illustrated in FIG. 12, by microfabrication techniques known to those of skill in the relevant art. Thus, lens regions 186 correspond to a first optical subsystem, while lens regions 187 correspond to a second optical subsystem; adjustment of the transmissivities of lens regions 186 to provide full transmissivity while adjusting the transmissivities of lens regions 187 to substantially-zero transmissivity thus routes the visual input through the first optical subsystem. Conversely, adjustment of the transmissivities of lens regions 186 to provide substantially zero transmissivity while adjusting the transmissivities of lens regions 187 to full transmissivity routes the visual input through the second optical subsystem. Different interleaving patterns can support three or more different optical subsystems.

Switching between two or more optical subsystems according to either of the above described methods could be controlled manually by the subject, by pushing a button or intentionally generating a readily detected control signal (a blink, etc.) or controlled automatically in response to vergence movement of eyes, change in distance to the visual target (detected, for example, by a rangefinder), or a sufficiently large change in focal quality of the detected image. According to either of the above embodiments, one or more of the optical subsystems may be adjusted to the current state of the visual input and the eye optics of the subject in order to compensate for gradual changes in imaged focal quality, while switching between the subsystems may be used to compensate for more abrupt changes (for example, when the subject switches abruptly from a near vision task, such as reading the dashboard display of a car, to a distance vision task, such as looking at the road ahead).

Various components of the system, including the adjustable lens system, processor, and input and output image detectors may require some form of power supply. While the invention is not limited to any particular type of power supply, if the power supply is to be included in an eyeglass frame, contact lens, or intraocular lens, it will typically be small and lightweight. For embodiments in which the adjustable lens system is mounted in an eyeglass frame, the device may be conveniently powered by a battery. Photovoltaic cells may also be used to provide power to the device. The power supply and possibly other components of the device as well may be located at a distance from the adjustable lens system, and power transmitted to the device, e.g. by inductive coupling or by power-beaming. The power supply may include an inductive coil or an antenna.

In some embodiments, the body of the subject may be used as a power source for powering the device. Various "energy scavenging" or "energy harvesting" devices are known, or may be developed (see e.g., U.S. Pat. Nos. 6,615,074, 6,655,035 and 6,768,246, and published U.S. Patent applications 20030014091 and 20030165648, all of which are incorporated herein by reference). For example, devices that capture energy from body movement of the subject (e.g., inertial devices as are used to power self-winding wristwatches) may be used to power the device. Pressure and chemical gradients within the body may also provide energy for powering operation of the device. For example, energy may be captured from the systolic-diastolic cycle or pulsatile blood flow of the subject, or through a micro-turbine or powered shunt placed in the respired airflow of the subject. Although reference has been made to a single power supply, the invention is not limited to use of a single power supply, and the invention includes embodiments in which separate power supplies may be used for different parts of the system or during different circumstances of operation of the system, or both. Various components of the system may have different power sources in the system as a whole, may have one or multiple power sources of various types and is not limited to any specific power source configuration.

Figure 13:
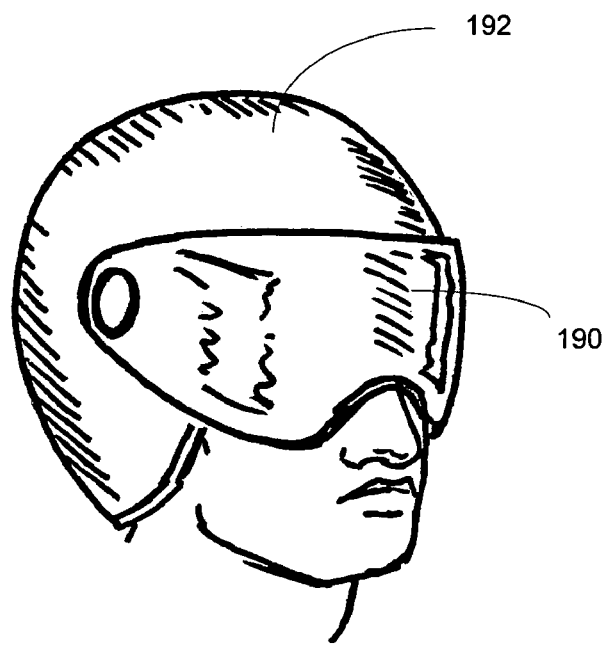
FIG. 13 shows a helmet-mounted embodiment.
Figure 14:
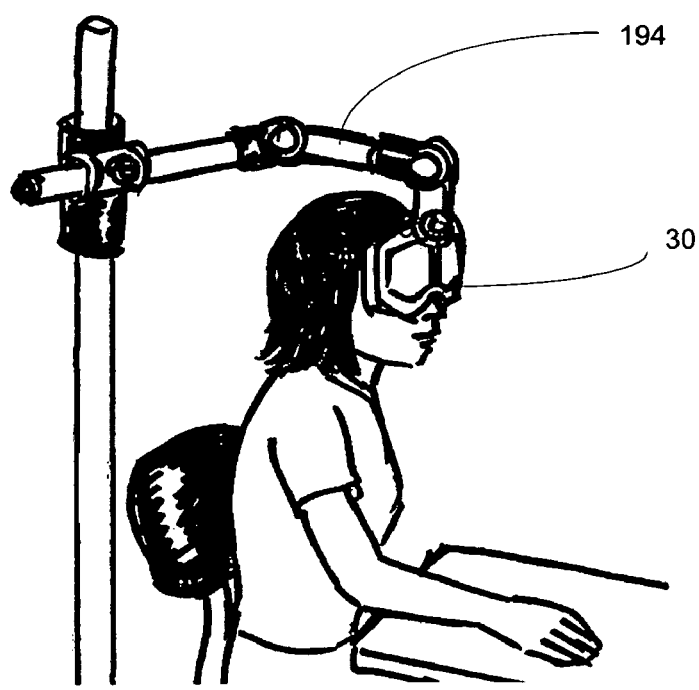
FIG. 14 shows implementation in an alternative mounting.

As depicted in FIG. 2, adjustable lens system 26 may be positioned with respect to eye 10 of the subject 28 via mounting 30. Mounting 30 may take various forms, examples of which are illustrated in FIGS. 13 and 14. Mounting 30 may be an eyeglass frame, as depicted previously in FIG. 2, or helmet mounted frame 190, as in FIG. 13. Helmet 192 may be of the type worn by an airplane pilot, for example. Alternatively, mounting 30 may include a mechanical linkage 194 secured to a wall or ceiling or mounted on a base set on a table or floor, such that, in use, the subject stands or sits, and the equipment is held in fixed relationship to the subject's eye, but is not attached directly to the subject's head. In general, as used herein, the term 'base' refers to any support or positioning structure to which mounting 30 is connected by a linkage in order to maintain the lens or optical system in proper relation to the subject's eye. As with the embodiments of the system in which mounting 30 is an eyeglass frame, other components of the system may be mounted on the mounting, or may be packaged separately.

The adjustable lens system may be implemented in the form of an eyeglass lens, a contact lens, or intraocular lens. The adjustable lens system (or at least a portion thereof) may be formed in, on, or in spatial association with such lenses, including placement behind or in front of such lenses, in addition to being housed in or formed integrally with such lenses. It may also be implemented in other forms; as depicted in FIGS. 13 and 14 it may be mounted in a helmet or in a stationary mount of the type used for optometric devices. The latter implementations are bulkier and present greater flexibility with regard to choice of system components and integration thereof. Although a helmet is depicted in FIG. 13, it will be appreciated that optical system components may be positioned with respect to the head by a variety of head mounted devices or structures, including headbands, hats, and other head coverings, which may not only provide support to system components but also function as head apparel or adornment. For implementation of the system as eyeglasses, and more particularly in the form of a contact lens or intraocular lens, system components that are to be located in or on the lens (e.g., the lens actuator and possibly sensor for detecting a neural or neuromuscular signal) will preferably be very small, light weight and of modest time-averaged power demand. Certain components of the system may be packaged separately from the adjustable lens system, thereby reducing size and weight constraints. For example, certain components of the system can be packaged in a case that can be carried in, for example, the subject's pocket. Wireless transmission of data, control and power signals may be achieved via RF transmission or inductive coupling or beaming. Various portions of the system may also include transmission and receiving devices to provide for sending signals between physically separated system components. Digital signals are thought to be particularly suited for effectively error-free transmission in such embodiments, but the practice of the methods herein are not limited to any particular method of data transmission. For eyeglass, helmet, or stationary mount devices, wiring may be satisfactory for carrying power and data and control signals.

With regard to the hardware and/or software used in neural signal detection and analysis, as well as various aspects of device control, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory semiconductor devices; and transmission type media such as digital and analog communication links using TDM or IP-based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for neural and/or neuromuscular signal detection and analysis, optical system control, and/or processes in the fashion set forth herein, and thereafter use standard engineering practices to integrate such described devices and/or processes into vision enhancement systems as exemplified herein. That is, at least a portion of the devices and/or processes described herein can be integrated into a vision enhancement system via a reasonable amount of experimentation. Those having skill in the art will recognize that such systems generally include one or more of a memory element such as volatile and/or non-volatile semiconductor-based memory, processors such as microprocessors and digital signal processors, computational-supporting or -associated entities such as operating systems, user interfaces, drivers, sensors, actuators, applications programs, one or more interaction devices, such as data ports, control systems including feedback loops and control-implementing actuators (e.g., devices for sensing position and/or velocity and/or acceleration or time-rate-of-change thereof; control motors for moving and/or adjusting components and/or quantities). A typical vision enhancement system may be implemented utilizing any suitable available components, such as those typically found in appropriate computing/communication systems, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of adjustable lens system configuration and neural or neuromuscular signal sensor configuration may be within the scope of the invention. As has been discussed, the choice of system configuration may depend on the intended application of the system, the environment in which the system is used, cost, personal preference or other factors. Image analysis and lens system control processes may be modified to take into account choices of lens system and image detector configuration, and such modifications, as known to those of skill in the arts of image analysis, control system design, and other relevant arts, may fall within the scope of the invention. Therefore, the full spirit or scope of the invention is defined by the appended claims and is not be limited to the specific embodiments described herein.

The invention claimed is:

1. A method of enhancing the vision of a subject with a vision modification system including an adjustable lens system, comprising the steps of:
   a) detecting a neuromuscular signal from a nerve or a muscle of the subject;
   b) inferring a focal condition based upon said detected neuromuscular signal, wherein there is a known relation between said focal condition and a state of focus of a visual input to an eye of said subject;
   c) adjusting the adjustable lens system in response to said focal condition in order to modify said visual input; and
   d) repeating steps a) through c) with said vision modification system in order to provide ongoing adaptive vision enhancement to said subject.

2. The method of claim 1, further comprising inferring the known relation between said focal condition and the state of focus of said visual input by a protocol comprising:
   a) delivering a series of well-defined visual inputs of varying state of focus;
   b) detecting a series of neuromuscular signals produced in response to said series of well-defined visual inputs;
   c) detecting a focal condition of said series of neuromuscular signals; and
   d) inferring a relation between said state of focus of said visual inputs and said focal condition of said neuromuscular signals.

3. The method of claim 2, including performing said protocol prior to providing ongoing adaptive vision enhancement to said subject.

4. The method of claim 2, including performing said protocol at intervals while providing ongoing adaptive vision enhancement to said subject.

5. The method of claim 1, including detecting said neuromuscular signal from a nervous system of said subject.

6. The method of claim 1, including detecting said neuromuscular signal from at least one motor nerve of said subject.

7. The method of claim 1, wherein said neuromuscular signal is an electromyographic signal.

8. The method of claim 1, including detecting said neuromuscular signal from at least one of an extraocular muscle, a ciliary muscle, an iris, and a facial muscle of said subject.

9. The method of claim 1, wherein said detected neuromuscular signal is an optoelectronic measure of neuromuscular activity.

10. The method of claim 9, wherein said detected neuromuscular signal is detected using near infrared imaging.

11. The method of claim 10, wherein said detected neuromuscular signal is an optoelectronic measure of at least one indicator of metabolic activity in a neuromuscular structure.

12. The method of claim 10, wherein said detected neuromuscular signal is an optoelectronic measure of at least one aspect of blood flow in a neuromuscular structure.

13. The method of claim 1, wherein adjusting said adjustable lens system includes adjusting a chromatic aberration correction of said adjustable lens system.

14. The method of claim 1, wherein adjusting said adjustable lens system includes adjusting a transverse position of said adjustable lens system with respect to an optical axis of said eye.

15. The method of claim 1 wherein adjusting said adjustable lens system includes adjusting an effective aperture of said adjustable lens system.

16. The method of claim 1, wherein adjusting said adjustable lens system includes adjusting a transmissivity of said adjustable lens system in at least one spectral waveband.

\* \* \* \* \*